United States Patent [19]
Froimowitz et al.

[11] Patent Number: 6,011,070
[45] Date of Patent: Jan. 4, 2000

[54] SLOW-ONSET, LONG-LASTING DOPAMINE REUPTAKE BLOCKERS

[75] Inventors: Mark Froimowitz, Newton; Kuo-Ming Wu, Acton, both of Mass.

[73] Assignee: Allelix-Pharm-Eco L.P., Lexington, Mass.

[21] Appl. No.: 08/911,778

[22] Filed: Aug. 15, 1997

Related U.S. Application Data

[60] Provisional application No. 60/024,099, Aug. 16, 1996.

[51] Int. Cl.$^7$ .................................................. A61K 31/135
[52] U.S. Cl. ............................................................ 514/657
[58] Field of Search .............................................. 514/657

[56] References Cited

U.S. PATENT DOCUMENTS 5,639,913   6/1997   Lidor et al. ............................ 564/304

FOREIGN PATENT DOCUMENTS

| 076 669 | 10/1982 | European Pat. Off. . |
| 2339715 | 2/1975 | Germany . |
| WO95/18617 | 7/1995 | WIPO . |

OTHER PUBLICATIONS

S. Rosonzweig–Lipson et al., "Stereoselective Behavioral Effects of Lu 19–005 in Monkeys: Relation to Binding at Cocaine Recognition Sites," *Psychopharmacology*, 107:186–194 (1992).

K. P. Bogeso, et al., 3–Phenyl–1–Indanamines Potential Antidepressant Activity and Potent Inhibition of Dopamine, Norepinephrine and Serotonin Uptake, *J. Med. Chem.*, 28:1817–1828 (1985).

S. Izenwasser, et al., "Differential Relationships Among Dopamine Transporter Affinities and Stimulant Potencies of Various Uptake Inhibitors," *European Journal of Pharmacology*, 263:277–283 (1994).

N. Tomita, "Structure—Activity Relationships of Dopamine—and Norepinephrine–Uptake Inhibitors," *Chem. Pharm. Bull.* 38(6):1563–1569 (1990).

M. Froimowitz, et al., "Slow Onset, Long Lasting Dopamine Reuptake Blockers as Potential Medications for the Treatment of Cocaine Abuse," 1996 Annual Meeting, Washington, D.C., Nov. 16–21, 1996, Abstract, Mail Date: Aug. 18, 1996.

M. Froimowitz, et al., "Effects of a Slow–Onset, Long–Acting Dopamine Reuptake Blocker on Cacaine Self–Administration and on Nucleus Accumbens Dopamine," Society for Neuroscience Abstracts, vol. 23, Part. 1, 27$^{th}$ Annual Meeting, New Orleans, LA, Oct. 25–30, 1997, Mail Date: Aug. 25, 1997.

Eliot L. Gardner, et al., Poster presented at meetings of The College on Problems of Drug Dependence, Nashville, Tennessee, Jun. 1997.

*Primary Examiner*—Phyllis G. Spivack
*Attorney, Agent, or Firm*—Hamilton, Brook, Smith & Reynolds, P.C.

[57] ABSTRACT

Disclosed is a method of treating an individual who abuses cocaine by administering to the individual a therapeutically effective amount of an N,N-dialkyl 3-phenyl-1-indanamine or a mixture of N,N-dialkyl 3-phenyl-1-indanamines. Also disclosed is a method of treating an individual with Parkinson's disease or attention deficit hyperactivity disorder by administering to the individual a therapeutically effective amount of an N,N-dialkyl 3-phenyl-1-indanamine or a mixture of N,N-dialkyl 3-phenyl-1-indanamines.

27 Claims, 19 Drawing Sheets

SLOW-ONSET, LONG-LASTING DOPAMINE REUPTAKE BLOCKERS

RELATED APPLICATIONS

This application claims priority to U.S. Ser. No. 60/024,099, filed Aug. 16, 1996, the teachings of which are incorporated herein by reference.

GOVERNMENT FUNDING

This invention was made with Government support under Contract No. NO1DA-4-8313 awarded by the National Institute on Drug Abuse. The Government has certain rights in the invention.

BACKGROUND OF THE INVENTION

Drug abuse is a pervasive problem in modern society. The most abusable and addictive drugs are those which have fast onsets and short durations of action. Cocaine, for example, has an onset of action on the order of seconds and of synaptic dopamine and this is associated with feelings of euphoria and well being. While the immediate, short term effect of cocaine is to increase synaptic levels of dopamine, chronic use of cocaine may result in depleted levels of synaptic dopamine in the absence of cocaine. This has been associated with ahedonia and chronic cocaine craving upon cessation of cocaine use.

One strategy for treating cocaine abusers is to administer an alternative dopamine reuptake blocker which will raise synaptic levels of dopamine. Known methods for raising reduced levels of synaptic dopamine and thus, reducing the craving for cocaine, include the use of compounds that block dopamine reuptake. (Rosenzweig-Lipson et al., *Psychopharmacology* 10:186 (1992)). However, even these dopamine reuptake blockers are limited to a duration of between about two and four days (Rosenzweig-Lipson et al., *Psychopharmacology* 10:186 (1992)). Even a duration of two to four days requires a relatively regimented schedule for patients, who, because of their affliction, may not adhere to the prescribed dosages.

There is a continuing need for new medications for the treatment of cocaine abuse. Further, drugs which block the reuptake of dopamine are also believed to have other potential utilities such as for the treatment of attention deficit hyperactivity disorder and Parkinson's disease.

SUMMARY OF THE INVENTION

The present invention is a method of treating an individual who abuses cocaine with N,N-dialkyl 3-phenyl-1-indamines. Novel N,N-dialkyl 3-phenyl-1-indanamines are reported in the co-pending U.S. patent application filed on Aug. 15, 1997, entitled NOVEL COMPOUNDS FOR TREATING COCAINE ABUSE Ser. No. 08/911,864, the entire teachings of which are incorporated herein by reference.

In one embodiment the present invention is a method of treating an individual for cocaine abuse. The method comprises administering to the individual a therapeutically effective amount of a compound or mixture of compounds represented by Structural Formula (I):

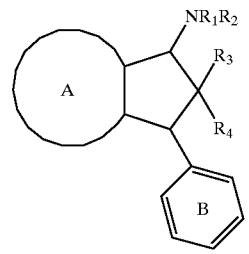

Ring A is selected from the group consisting of an aryl group, a substituted aryl group, a heteroaryl group and a substituted heteroaryl group. Ring A is preferably phenyl, naphthyl or indolyl. More preferably, Ring A is phenyl.

R1 is selected from the group consisting of a lower alkyl group and a substituted lower alkyl group. Preferably, R1 is methyl.

R2 is selected from the group consisting of a lower alkyl group, a substituted lower alkyl group, —$(CH_2)_n$-aryl and —$(CH_2)_n$-(substituted aryl), wherein n is an integer from one to about 3. Preferably, R2 is a benzyl group. Alternatively, R2 is preferably a C1 to C4 straight or branched chain lower alkyl group, for example, methyl, ethyl, n-propyl, iso-propyl, n-butyl, sec-butyl or t-butyl.

R3 and R4 are independently selected from the group consisting of —H, a lower alkyl group and a substituted lower alkyl group. R3 and R4 are preferably each —H.

Ring B is unsubstituted or substituted with one, two or three substituents other than hydrogen. Suitable substituents include halogen, an alkyl group, a substituted alkyl group, hydroxy, (lower alkyl)-O—, (substituted lower alkyl)-O—, —CN, —$NO_2$, amine, (lower alkyl) amine, (substituted lower alkyl) amine, (di-lower alkyl) amine and (substituted di-lower alkyl) amine.

In another embodiment the present invention is a method of treating an individual with a disease involving depletion of synaptic dopamine. Examples include cocaine abuse, Parkinson's disease or attention deficit hyperactivity disorder. The method comprises administering to the individual a therapeutically effective amount of a compound or a mixture of compounds represented by Structural Formula (I).

The methods of treating cocaine abuse, Parkinson's disease and attention deficit hyperactivity disorder disclosed herein utilize compounds which block the reuptake of dopamine and which have a slow onset of action. Thus, the abuse potential by individuals being treated is minimized compared with drugs which have a more rapid onset of activity. For example, reported herein are results showing that N,N-dialkyl 3-1-indanamines block the effects of cocaine in mammals. For example, N,N-dimethyl-3-(3',4'-dichlorophenyl)-1-indanamine, Compound 1, produces a dose-dependent decrease in cocaine self-administration in rhesus monkeys (Example 7) and Compounds 2 and 7 block cocaine induced locomotor activity in mice (Example 3).

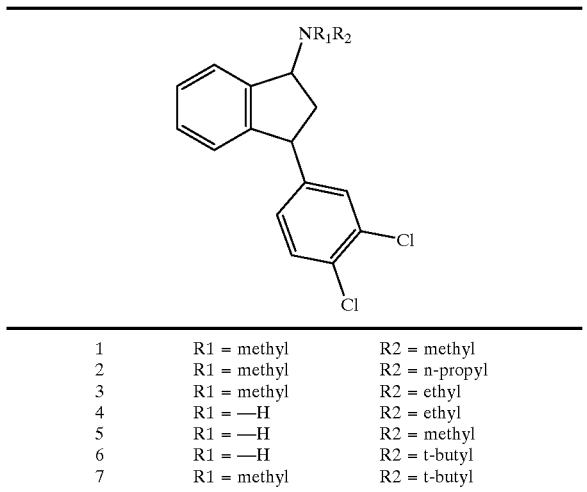

| | | |
|---|---|---|
| 1 | R1 = methyl | R2 = methyl |
| 2 | R1 = methyl | R2 = n-propyl |
| 3 | R1 = methyl | R2 = ethyl |
| 4 | R1 = —H | R2 = ethyl |
| 5 | R1 = —H | R2 = methyl |
| 6 | R1 = —H | R2 = t-butyl |
| 7 | R1 = methyl | R2 = t-butyl |

It has also been found that N,N-dialkyl 3-phenyl-1-indanamines, e.g., Compounds 1–3, stimulate locomotor activity when administered at levels of 10 mg/kg and less (Examples 2 and 5). Furthermore, the induction of activity is slow, occurring after twenty to thirty minutes (Example 2). Moreover, N,N-dialkyl 3-phenyl-1-indanamines are pharmacologically active for longer periods of time in mammals than N-monoalkyl 3-phenyl-1-indanamines. For example, Compound 1 has been found to stimulate locomotor activity in primates for five to seven days (Example 5), while Compound 5, its monoalkyl analog, stimulates locomotor activity for only about two to four days (Example 5).

The aforementioned results show that N,N-dialkyl 3-phenyl-1-indanamines are effective compounds in treating individuals who abuse cocaine.

In addition, these compounds can also be used as drugs with long-lasting effects for individuals who require treatment with dopamine reuptake blockers, for example, individuals with Parkinson's disease or attention deficit hyperactivity disorder. Because of the long duration of action of the compounds utilized in the methods of treatment, the intervals between dosing can be lengthened compared with drugs having a shorter duration of action.

DETAILED DESCRIPTION OF THE INVENTION

Figure 1:
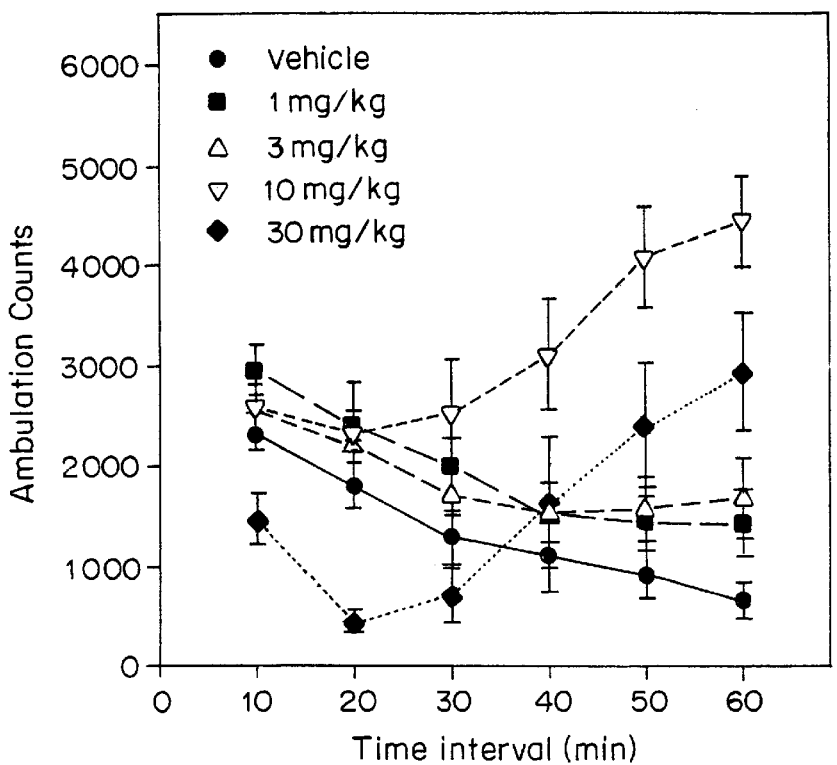
FIG. 1 is a graph showing the number of ambulation counts resulting from the stimulation of locomotor activity in mice over time by the administration of 1) vehicle; 2) 1 mg/kg of Compound 1; 3) 3 mg/kg of Compound 1; 4) 10 mg/kg of Compound 1; and 5) 30 mg/kg of Compound 1.
Figure 2:
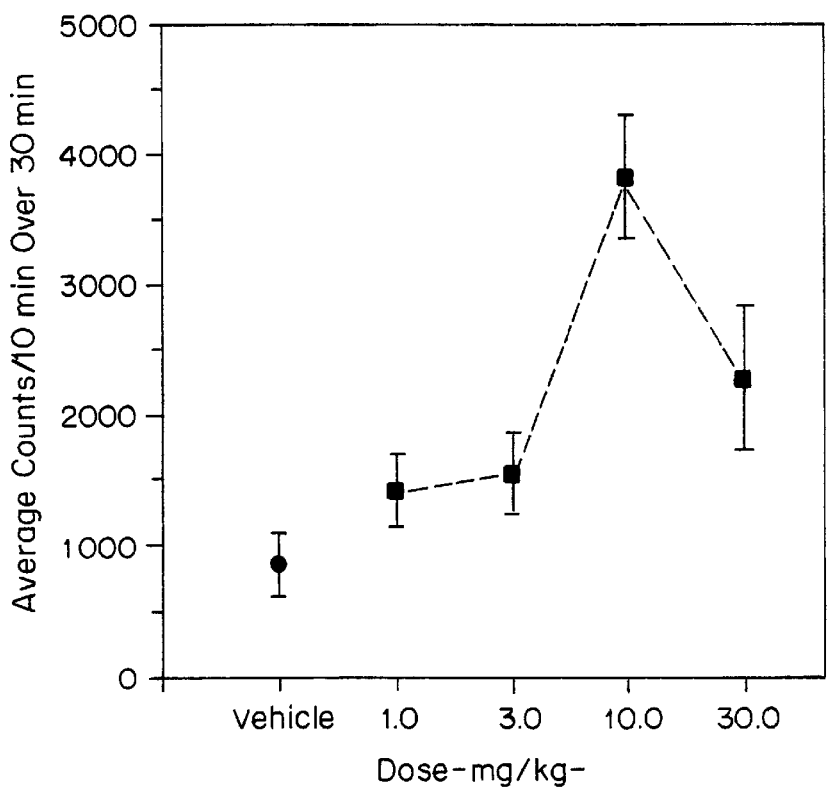
FIG. 2 is a graph showing the average number of ambulation counts/10 minutes over 30 minutes resulting from the stimulation of locomotor activity in mice versus the dosage of Compound 1 administered to the mice.
Figure 3:
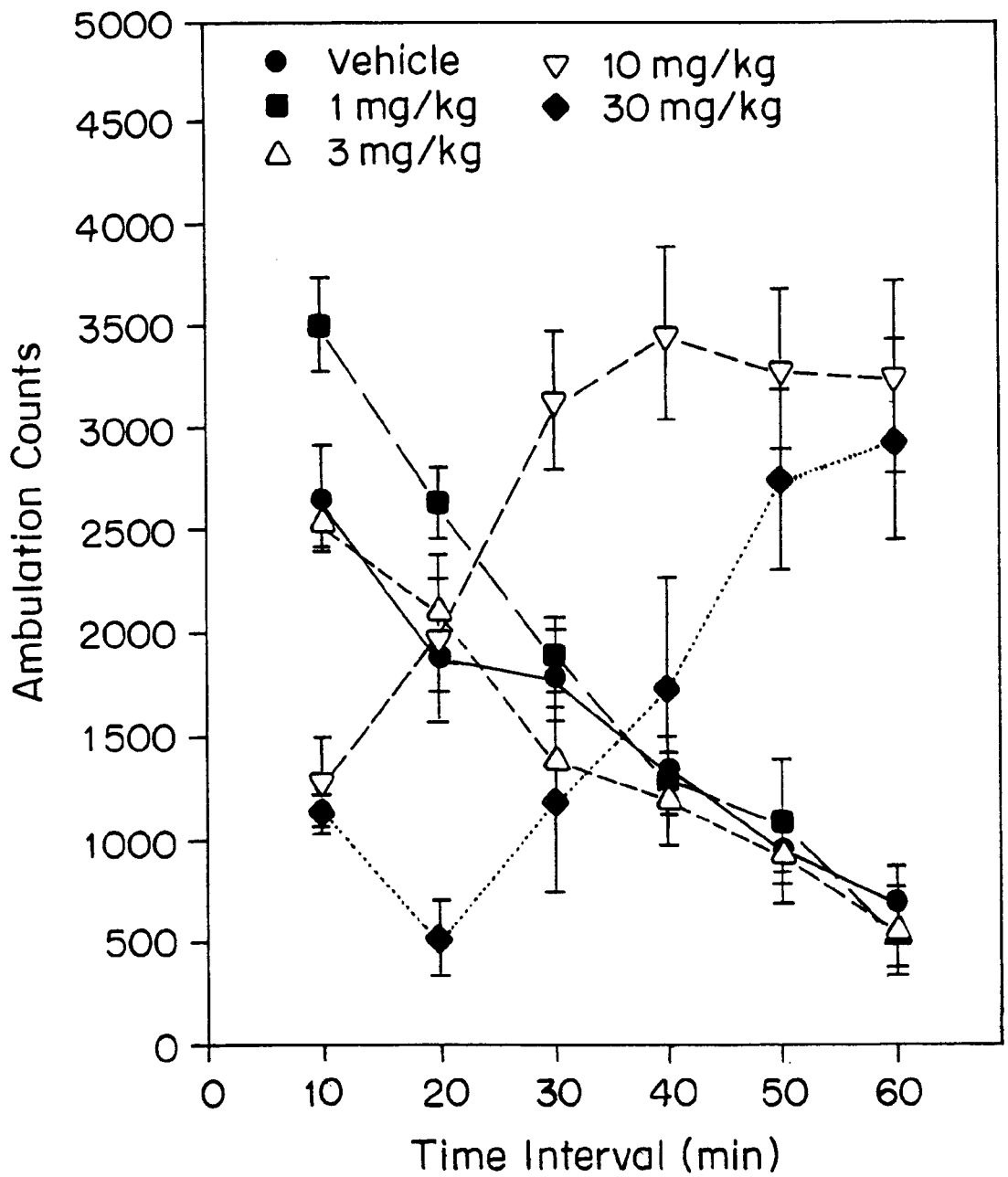
FIG. 3 is a graph showing the number of ambulation counts resulting from the stimulation of locomotor activity in mice over time by the administration of 1) vehicle; 2) 1 mg/kg of Compound 2; 3) 3 mg/kg of Compound 2; 4) 10 mg/kg of Compound 2; and 5) 30 mg/kg of Compound 2.
Figure 4:
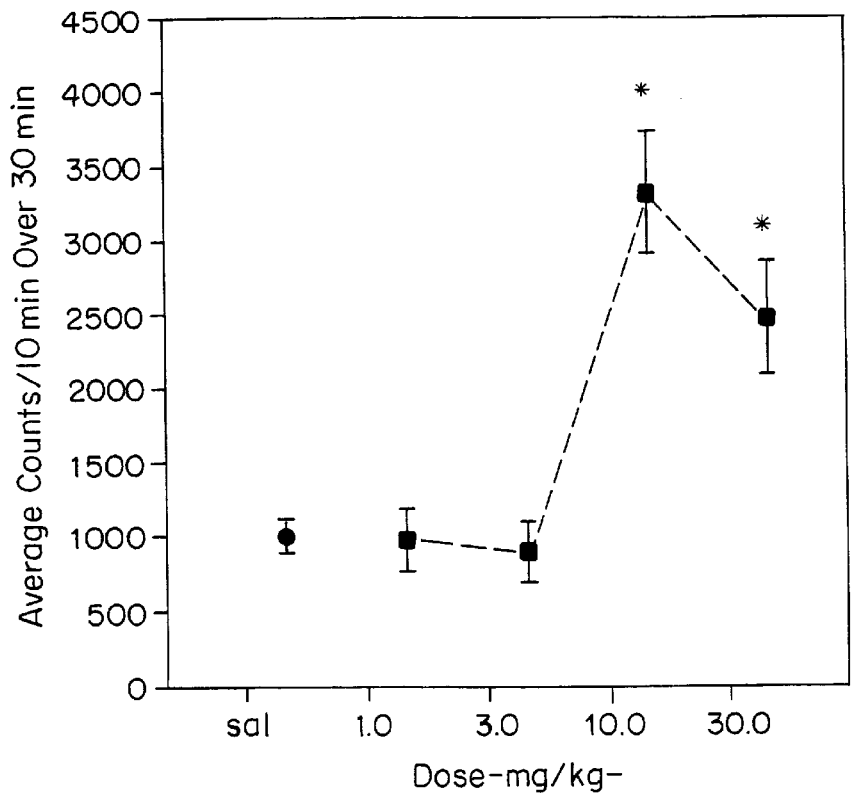
FIG. 4 is a graph showing the average number of ambulation counts/10 minutes over 30 minutes resulting from the stimulation of locomotor activity in mice versus the dosage of Compound 2 administered to the mice.
Figure 5:
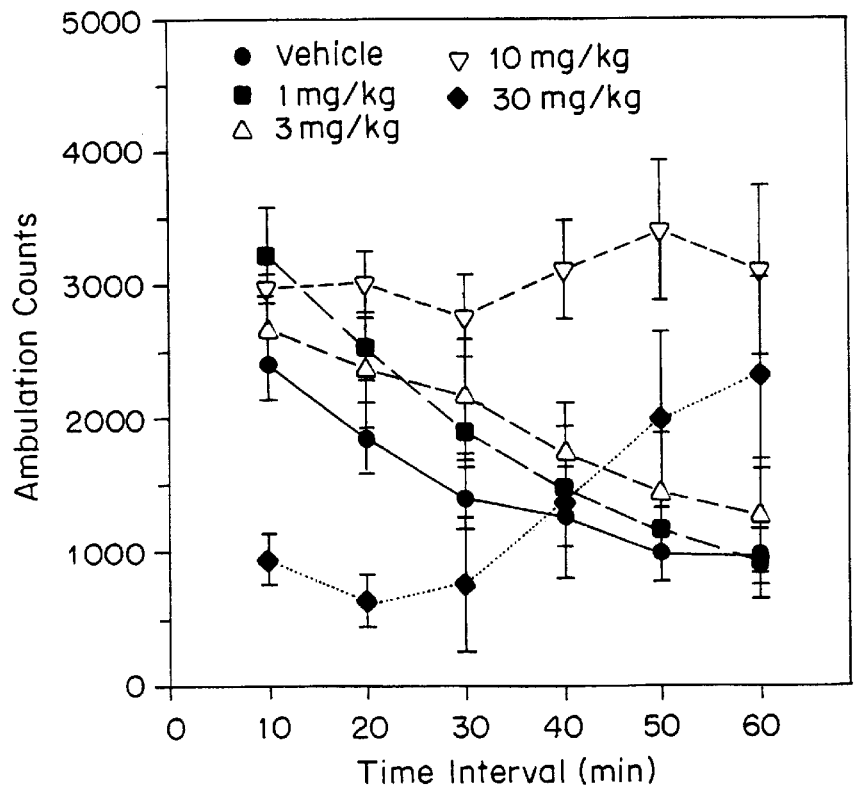
FIG. 5 is a graph showing the number of ambulation counts resulting from the stimulation of locomotor activity in mice over time by the administration of 1) vehicle; 2) 1 mg/kg of Compound 3; 3) 3 mg/kg of Compound 3; 4) 10 mg/kg of Compound 3; and 5) 30 mg/kg of Compound 3.
Figure 6:
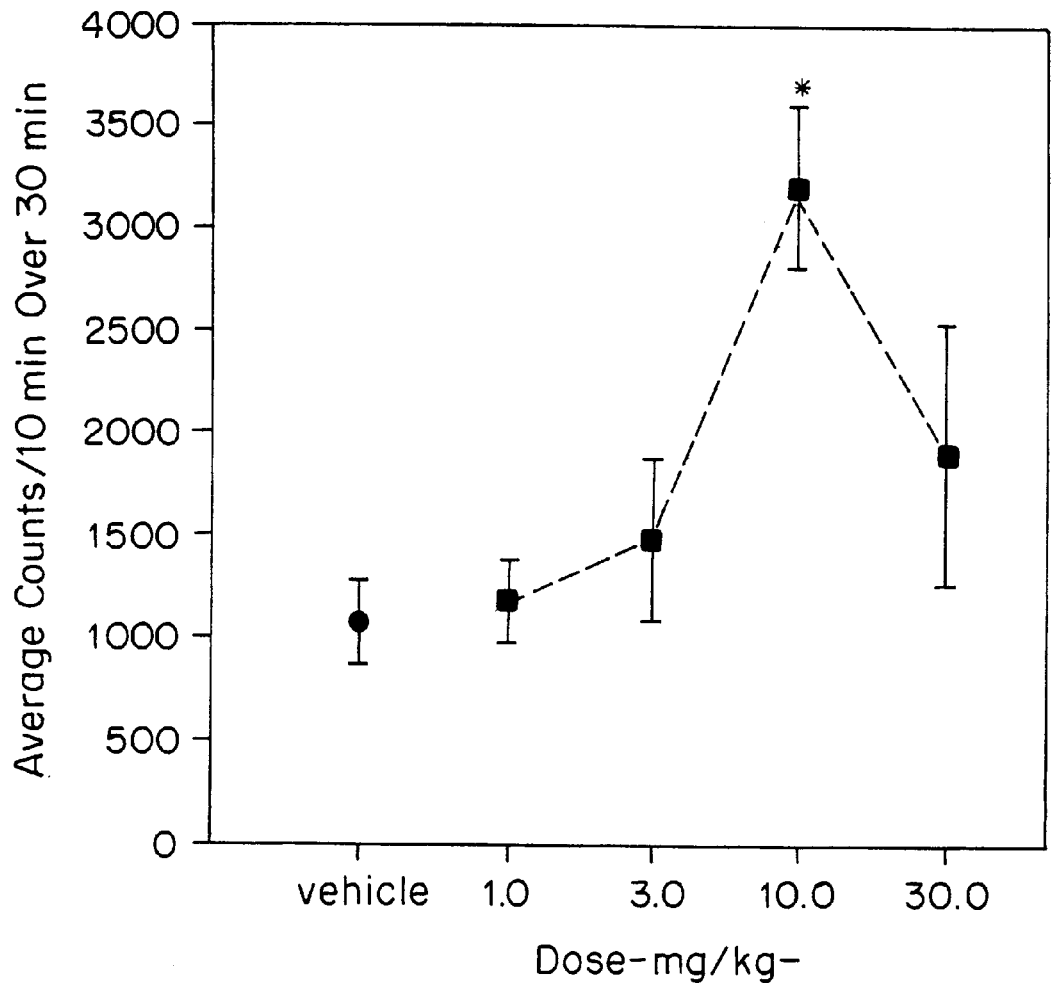
FIG. 6 is a graph showing the average number of ambulation counts/10 minutes over 30 minutes resulting from the stimulation of locomotor activity in mice by Compound 3 versus the dosage of Compound 3 administered to the mice.
Figure 7:
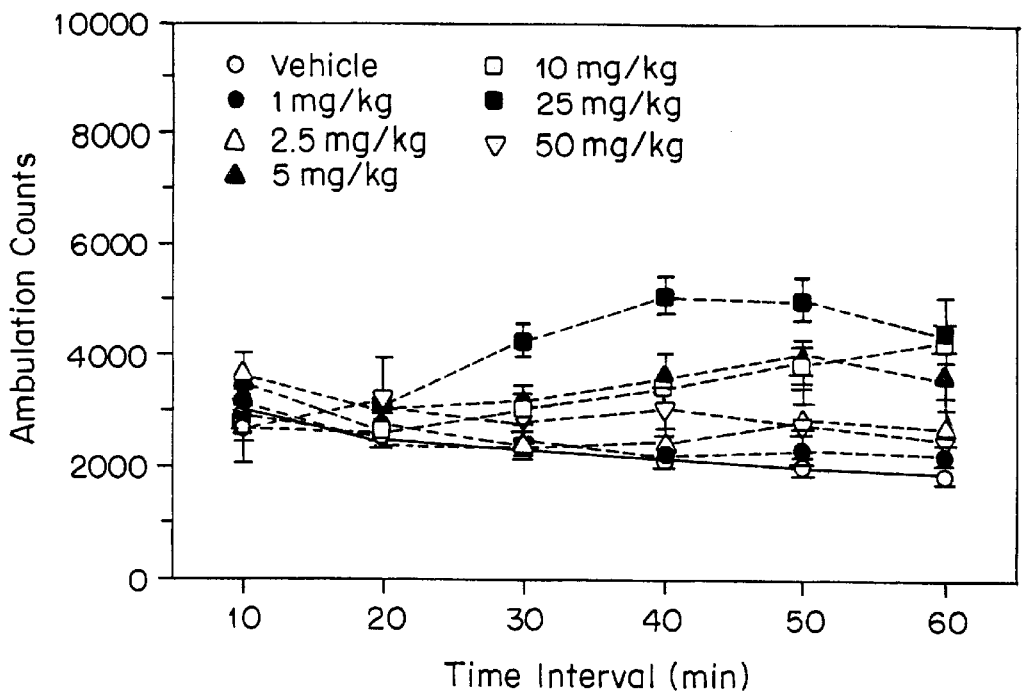
FIG. 7 is a graph showing the number of ambulation counts resulting from the stimulation of locomotor activity in mice over time by the administration of 1) vehicle; 2) 1 mg/kg of Compound 4; 3) 3 mg/kg of Compound 4; 4) 10 mg/kg of Compound 4; and 5) 30 mg/kg of Compound 4.
Figure 8:
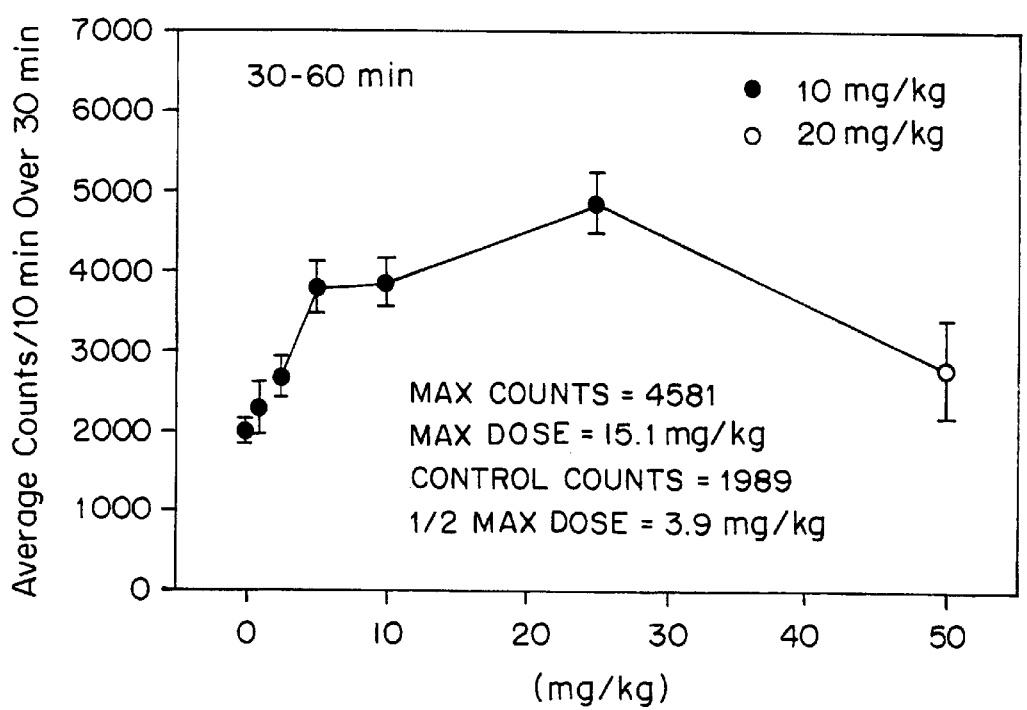
FIG. 8 is a graph showing the average number of ambulation counts/10 minutes over 30 minutes resulting from the stimulation of locomotor activity in mice 4 versus the dosage of Compound 4 administered to the mice.

In a preferred embodiment, the compound used in the methods of treatment is represented by Structural Formula (II):

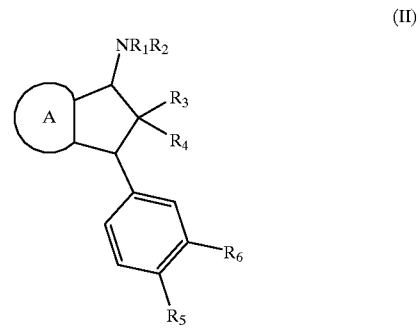

(II)

R2 is a lower alkyl group or a substituted lower alkyl group, preferably a C1 to C4 straight or branched chain alkyl group. Ring A, R1 and R3–R4 are as described for Structural Formula (I). R5 and R6 are each —H or a substituent, as described for Ring B in Structural Formula (I).

In a more preferred embodiment, the compound used in the methods of treatment is represented by Structural Formula (III):

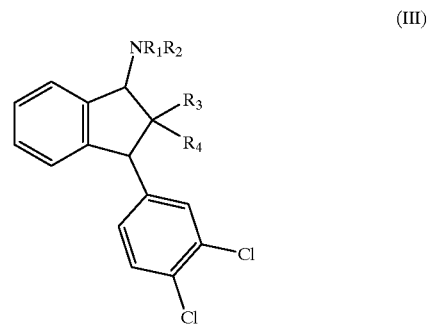

(III)

R1–R4 are as defined above for Structural Formula (II). In Structural Formula (III), R3 and R4 are preferably each —H and the compound is in the trans configuration. Examples include wherein R1 is methyl, R2 is selected from the group consisting of methyl, ethyl and propyl and R3 and R4 are each —H. Other examples include wherein R1 is methyl, R2 is n-butyl, sec-butyl or tert-butyl and R3 and R4 are each —H.

In another preferred embodiment, the compound used in the methods of treatment is represented by Structural Formula (II), wherein R2 is a benzyl group or a substituted benzyl group, preferably a benzyl group. Ring A, R1 and R3–R6 are as described for Structural Formula (II).

In a more preferred embodiment, the compound used in the methods of treatment is represented by Structural Formula (III), wherein R2 is a benzyl group or a substituted benzyl group, preferably a benzyl group. R1 and R3—R4 are as described above for Structural Formula (III). R3 and R4 are preferably each —H and the compound is in the trans configuration. Examples include wherein R1 is methyl, R2 is benzyl and R3 and R4 are each —H.

An "aryl group" includes carbocyclic aromatic structures. An "aryl group" can be monocyclic (e.g., phenyl) or polycyclic. A polycyclic aromatic group includes moieties having one or more fused carbocyclic aromatic structures, e.g. naphthyl or anthracyl.

Suitable heteroaryl groups include monocyclic or polycyclic aromatic groups containing one or more heteroatoms such as oxygen, nitrogen or sulfur. Suitable monocyclic heterocyclic groups include imidazolyl, thienyl, pyridyl, furanyl, oxazoyl, pyrollyl, pyrimidinyl, furanyl, pyrazolyl, pyrrolyl, thiazolyl and the like. A polycyclic heteroaryl group includes fused structures such as quinonyl, isoquinonyl, indoyl benzimidazoyl, benzothiazolyl, benzothiophenyl, benzofuranyl and benzopyranyl.

A "lower alkyl group" includes C1 to about C10 straight or branched chain hydrocarbons. The hydrocarbon can be saturated or can have one or more units of unsaturation. Preferred lower alkyl groups are straight chain C1–C3 hydrocarbons. Alternatively, lower alkyl groups preferably include C1 to C4 straight chain and branched hydrocarbons.

Suitable substituents for an aryl, heteroaryl, benzyl or lower alkyl group include substituents which do not signifiantly decrease the affinity of the N,N-dialkyl 3-phenyl-1-indanamine for the dopamine transporter or the bioavailability of the N,N-dialkyl 3-phenyl-1-indanamine. Suitable examples include halogens, lower alkyl, hydroxy, (lower alkyl)-O—, (substituted lower alkyl)-O—, —CN, —NO$_2$, —NH$_2$, (lower alkyl)NH—, (substituted alkyl)NH—, dialkylamine and (substituted dialkyl)amine.

In the method of treatment disclosed herein the trans stereoisomer of the compound represented by Structural Formula (I) is preferentially administered. Examples of cis and trans stereoisomers are shown below.

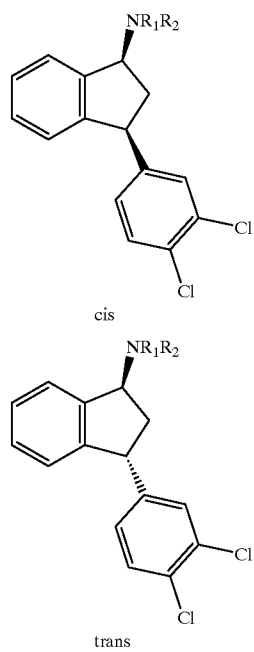

The compound can be administered as a racemic mixture of enantiomers, as an optically pure enantiomer or as a mixture enriched in one enantiomer.

A "therapeutically effective" amount of a compound is the amount of compound which decreases or alleviates the severity of the symptoms associated with a disease, e.g., Parkinson's disease, attention deficit hyperactivity disorder or cocaine abuse, in an individual being treated with the compound. In the case of treatment of cocaine abuse, a "therapeutically effective" amount of a compound can be the amount of compound which decreases the craving for cocaine of an individual who abuses cocaine. Typically, a "therapeutically effective amount" of the compound ranges from about 1 mg/day to about 1000 mg/day.

The compounds of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to capsular and tablet formulations (for oral and rectal administration), liquid formulations (for oral, intravenous, intramuscular or subcutaneous administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles may include saline, sterile water, distilled water, Ringer's solution, and isotonic sodium chloride solutions. The specific dosage level of active ingredient will depend upon a number of factors, including, for example, biological activity of the particular preparation, age, body weight, sex and general health of the individual being treated.

The pharmaceutical compositions used in the methods of treatment disclosed herein can contain one N,N-dialkyl 3-1-indanamine. Alternatively, the pharmaceutical composition can contain more than one N,N-dialkyl 3-1-indanamine, e.g. the individual is being administered a mixture of N,N-dialkyl 3-1-indanamines. When a mixture is being administered, virtually any ratio of N,N-dialkyl 3-phenyl-1-indanamines can be used that is non-toxic and therapeutically effective.

The compounds of the present invention used in the treatment of an individual with Parkinson's disease or attention deficit hyperactivity disorder can be co-administered with other pharmaceutically active agents used in the treatment of Parkinson's disease or attention deficit hyperactivity disorder. The compounds of the present invention used in the treatment of an individual who abuses cocaine can be combined with other therapies used to treat individuals who abuse cocaine. Such therapies can include the co-administration of other pharmaceutically active agents used to treat cocaine abuse or psychological therapies.

When the compounds of the present invention are used in combination with other pharmaceutically active agents, the specific combination will vary, depending on a number of factors, including, for example, activity of the agents, their side-effects, and the weight, age, sex and general health of the individual being treated.

The preparation of compounds of the present invention is shown in the Scheme and described more fully in Example 1. It is noted that compounds represented by Structural Formula (I) in which Ring A is an aryl group other than phenyl can be prepared by using the corresponding aryl aldehyde as a starting material in place of benzaldehyde. For example, compounds represented by Structural Formula (I) in which Ring A is a 1-naphthyl or 1-thiophene group can be prepared by using 1-CHO-napthalene or 1-CHO-thiophene as a starting material in place of benzaldehyde.

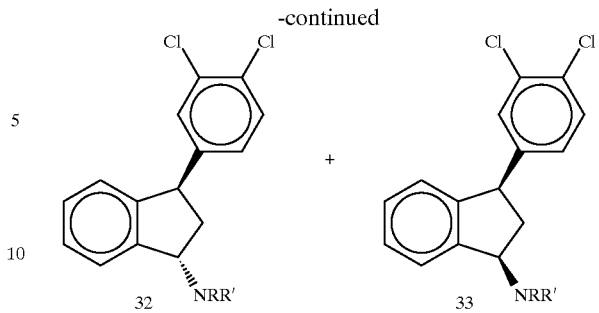

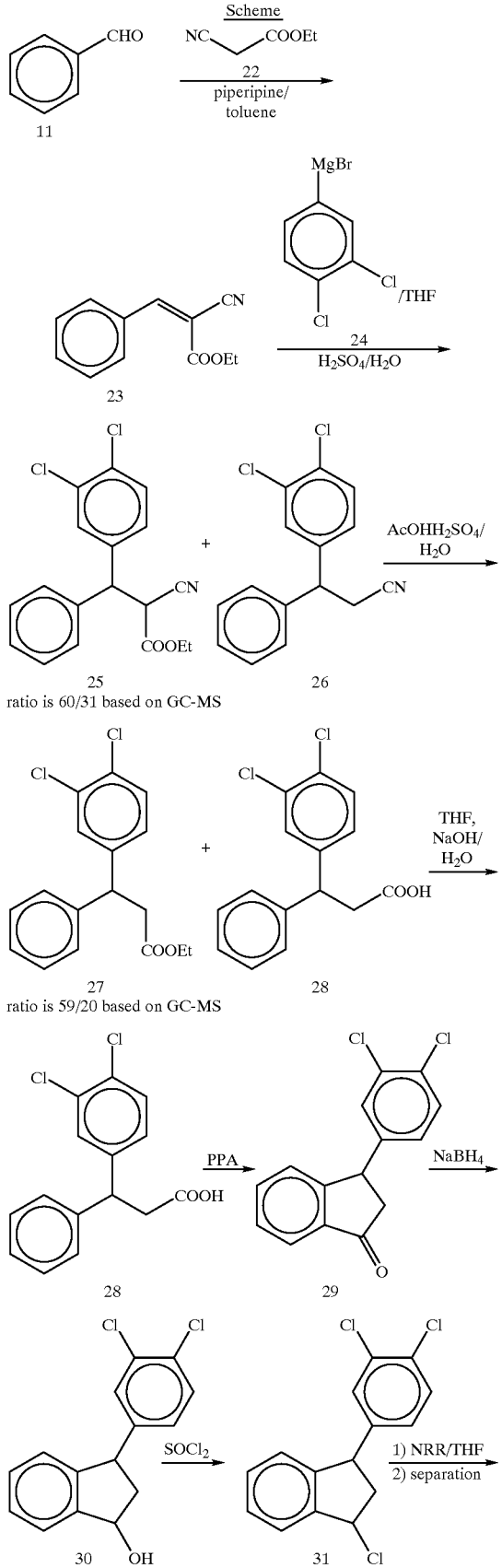

The invention is further illustrated by the following examples.

EXEMPLIFICATION

EXAMPLE 1

PREPARATION OF N,N-DIALKYL 3-PHENYL-1-INDANAMINES

PREPARATION OF COMPOUND 23

A solution of benzaldehyde (318 g) and ethyl cyanoacetate (383 g) in toluene (1.5 L) was brought to boiling in a flask equipped with a Dean-Stark trap. After ~60 mL of water was collected, the resulting mixture was concentrated under reduced pressure. Vacuum drying gave 690 g of a wet solid. Recrystallization from 1.5 L of THF and 3 L of hexanes gave a.pale-yellow solid (360 g).

PREPARATION OF COMPOUND 25

Magnesium turnings (6.7 g) were activated by heating with iodine (0.02 g) under an Ar atmosphere. After anhydrous THF (200 mL) was added, a solution of 1-bromo-3,4-dichlorobenzene (63.1 g) in anhydrous THF (100 mL) was added under Ar slowly so that gentle boiling was maintained. The resulting mixture was then brought to reflux for 0.5 hours. The resulting mixture was cooled to room-temperature and slowly added to a solution of 23 in anhydrous THF (100 mL) under Ar via cannula. The stirring was continued for 1 hour. The resulting mixture was poured onto a mixture of ice (200 g) and concentrated $H_2SO_4$ (10 mL). The organic layer was separated from the aqueous layer and the aqueous layer was extracted with EtOAc (2×100 mL). The combined EtOAc solution was washed with water (200 mL) and then with brine (200 mL). Solvent evaporation under reduced pressure followed by vacuum drying gave a thick orange oil (96.7 g).

PREPARATION OF COMPOUND 28

A mixture of crude 25 (96 g), AcOH (192 mL), $H_2SO_4$ (96 mL), and water (96 mL) was brought to reflux (20 hours). The resulting mixture was poured onto ice (200 g). The organic layer was separated from the aqueous layer and the aqueous layer was extracted with $CH_2Cl_2$ (200 mL). The combined organic solution was washed with water (200 mL) and then with brine (200 mL). Solvent evaporation under reduced pressure followed by vacuum drying gave a thick brown oil (87.4 g). THF (87 mL), NaOH (17.5 g) and water (87 mL) were added to the thick oil. The resulting mixture was brought to reflux for 2.5 hours. Water (87 mL) was added and the mixture was acidified with 37% HCl(aq) (50 mL, pH≦1). The organic layer was separated from the aqueous layer and the aqueous layer was extracted with EtOAc (87 mL). The combined organic solution was washed with water (200 mL) and then with brine (200 mL). Solvent evaporation under reduced pressure and vacuum drying provided a thick brown syrup (78.6 g).

PREPARATION OF COMPOUND 29

A mixture of the crude acid 28 (78.6 g) and polyphosphoric acid (225 g) was stirred under an Ar atmosphere for 3 hours at ~100° C. The resulting mixture was poured onto ice (225 g) and EtOAc (225 mL). The organic layer was separated from the aqueous layer and the aqueous layer was extracted with EtOAc (2×110 mL). The combined EtOAc solution was washed with water (110 mL) and brine (110 mL). Solvent evaporation under reduced pressure and vacuum drying gave a wet brown solid. A solution of the solid in $CH_2Cl_2$ was passed through a silica gel plug (9 in I.D., 3 in high) with $CH_2Cl_2$. Solvent evaporation of the collected fractions under reduced pressure followed by vacuum drying finishing with a wet brown solid (57.4 g).

PREPARATION OF COMPOUND 30

$NaBH_4$ (2.46 g) was added in three portions to a mixture of ketone 29 (56.6 g), EtOAc (260 mL), and EtOH (120 mL) with stirring under an Ar atmosphere. After 0.5 h, more $NaBH_4$ (0.5 g) was added and the stirring was continued for another 0.5 hours. Solvent evaporation under reduced pressure gave a thick dark brown oil. Water (260 mL) was added and the mixture was extracted with EtOAc (260 mL and then 2×80 mL). The combined organic solution was washed with brine and water. Solvent evaporation under reduced pressure gave a brown syrup, which was passed through a silica gel plug (9 in I.D., 3.5 in high) with 800 mL of 80% $CH_2Cl_2$/hexanes, followed by 500 mL of $CH_2Cl_2$, and then with 500 mL of 20% EtOAc/$CH_2Cl_2$. The fractions containing the desired alcohols were collected. Solvent evaporation under reduced pressure and vacuum drying gave a brown residue (46.8 g).

PREPARATION COMPOUND 31

$SOCl_2$ was slowly added with stirring to a solution of alcohol 30 (22.5 g) in anhydrous toluene (135 mL) under an Ar atmosphere. The stirring was continued for 2 hours. Water (135 mL) was added. The organic solution was washed with water (135 mL) and then with brine (70 mL). Solvent evaporation under reduced pressure and vacuum drying afforded a thick brown oil (13.7 g).

PREPARATION OF COMPOUNDS 32 AND 33

A mixture of chlorides 31 (48.9 g) and excess amine (dimethylamine, 61.9 g; typically, 6–9 equivalents) in anhydrous THF (260 mL) was heated in a bomb to 100–130° C. for 20 hours with stirring. The resulting material was cooled to $\leq 30°$ C. Saturated $Na_2CO_3$ (aq) (400 mL) was added and the organic layer was separated from the aqueous layer. The aqueous layer was extracted with EtOAc (150 mL). The combined organic solution was washed with brine (200 mL). Solvent evaporation under reduce pressure and vacuum drying gave a thick black oil (48.1 g). The resulting crude product was subjected to purification either by preparative TLC, chromatography, or HPLC with a partial purification either by a silica gel plug or salt formation beforehand. For the N,N-dimethylindanamines, the purification was done as described below. The HCl salt formation from the black oil in a mixture of EtOH, ether, and acetone gave an almond solid enriched with the cis-isomer. The freebase enriched with the trans-isomer were recovered by treatment with saturated $Na_2CO_3$ (aq). Maleic acid salt formation from the freebases using EtOAc, EtOH, acetones, hexanes and ether gave a maleic acid salt as a greenish almond solid. Freebase from the mother liquor was again recovered by treatment with saturated $Na_2CO_3$ (aq). The recovered freebase was partially purified by passing through a silica gel plug. The recovered freebase, the freebase from the HCl salt, and the freebase from the maleic acid salt were subjected to HPLC separation (Phenomenex Primesphere 5μ silica 110 column, 250×21.2 mm; UV, 268 nm; 0.05% $Et_2NH$/EtOAc, 10 mL/min; cis-isomer, 17 minutes; trans-isomer, 20 minutes) to give pure 32 and 33.

SALT FORMATION OF COMPOUNDS 32 AND 33

Freebases 32 and 33 were converted the their corresponding Hcl, maleic acid or oxalic acid salts. A typical HCl salt formation involved dissolving a freebase in ether, adding 1.1 equivalents of 1 M HCl ether with stirring, vacuum filtration of the resulting suspension, washing the solid with ether and vacuum drying at an appropriate elevated temperature. A typical maleic acid or oxalic salt formation involved dissolving a freebase in ErOH and ether, adding a solution of maleic or oxalic acid (1.05 mol equivalents) in EtOH with stirring, adding more ether to the resulting mixture, vacuum filtration, washing the solid with ether, and vacuum drying at an appropriate elevated temperature.

Compounds 2–7 were prepared as described above, except that dimethylamine was replaced with the appropriate amine in the reaction with chlorides 31. In addition, the corresponding N-methyl-N-iso-propyl (Compound 8), N-(n-propyl) (Compound 9) and N-methyl-N-benzyl (Compound 10) phenylindanamines were prepared by replacing dimethylamine with methyl(2-propyl)amine, n-propylamine or methyl(benzyl)amine, respectively, in the reaction with chlorides 31.

The chemical shifts observed in the $^{13}C$ NMR spectrum of the maleic acid salt of Compound 1 in DMSO-$d_6$ are as follows: 36.6, 40.4, 42.1, 70.5, 127.1, 128.4, 129.6, 130.0, 131.1, 131.7, 132.3, 132.6, 133.0, 137.5, 137.6, 146.9, 149.7, 169.1.

The chemical shifts observed in the $^{13}C$ NMR spectrum of the HCl salt of Compound 2 in DMSO-$d_6$ are as follows: 33.9, 34.1, 35.1, 36.6, 47.8, 48.0, 54.1, 56.7, 66.5, 68.4, 125.1, 125.3, 127.4, 127.5, 127.7, 128.2, 128.6, 128.62, 129.2, 129.27, 129.3, 129.9, 130.0, 130.26, 130.3, 130.5, 130.7, 130.8, 131.1, 131.2, 131.5, 135.4, 135.7, 145.3, 147.9, 148.5.

The chemical shifts observed in the $^{13}C$ NMR spectrum of the oxalic acid salt of Compound 3 in DMSO-$d_6$ are as follows: 11.6, 36.3, 36.7, 49.5, 49.7, 69.1, 127.0, 128.4, 129.5, 130.0, 13:1.0, 131.6, 132.0, 132.6, 132.9, 138.2, 147.4, 149.6, 166.5.

The chemical shifts observed in the $^{13}C$ NMR spectrum of the HCl salt of Compound 4 in DMSO-$d_6$ are as follows: 12.9, 39.4, 41.6, 49.2, 61.9, 126.5, 128.4, 129.1, 130.0, 131.0, 131.5, 131.7, 132.6, 133.0, 139.4, 146.6, 138.9.

The chemical shifts observed in the $^{13}C$ NMR spectrum of the HCl salt of Compound 5 in DMSO-$d_6$ are as follows: 31.7, 39.1, 49.1, 63.1, 126.9, 128.1, 129.2, 130.0, 131.0, 131.5, 131.8, 132.6, 133.0, 139.3, 146.9, 148.8.

The chemical shifts observed in the $^{13}C$ NMR spectrum of the HCl salt of Compound 6 in DMSO-$d_6$ are as follows: 25.6, 40.3, 47.9, 56.7, 57.8, 124.7, 126.8, 127.2, 128.2, 129.2, 129.7, 129.8, 130.8, 131.1138.5, 145.0, 147.0.

The chemical shifts observed in the $^{13}$C NMR spectrum of the HCl salt of Compound 7 in CDCl$_3$ are as follows: 25.3, 26.1, 29.4, 34.8, 37.0, 43.8, 48.7, 49.3, 64.4, 64.8, 65.7, 125.2, 126.4, 126.9, 127.1, 127.6, 128.1, 128.8, 129.2, 129.7, 130.0, 130.7, 130.87, 130.9, 131.0, 131.2, 132.7, 132.9, 135.8, 136.2, 143.0, 144.2, 145.2, 149.4.

The chemical shifts observed in the $^{13}$C NMR spectrum of the HCl salt of Compound 8 in DMSO-d$_6$ are as follows: 16.1, 17.3, 18.1, 18.6, 31.7, 32.1, 33.7, 37.7, 47.6, 47.9, 54.6, 56.1, 65.1, 65.8, 125.2, 127.2, 127.3, 127.5, 127.7, 128.2, 128.4, 129.2, 129.3, 129.8, 130.0, 130.2, 130.4, 130.76, 130.8, 131.1, 135.5, 136.5, 145.0, 145.4, 147.76, 148.9.

The chemical shifts observed in the $^{13}$C NMR spectrum of the HCl salt of Compound 9 in DMSO-d$_6$ are as follows: 11.0, 19.1, 37.6, 46.0, 47.4, 60.4, 125.0, 126.6, 127.3, 128.2, 129.2, 129.7, 129.9, 130.7, 131.1, 137.5, 145.1, 147.1.

The chemical shifts observed in the $^{13}$C NMR spectrum of the HCl salt of Compound 10 in DMSO-d$_6$ are as follows: 33.9, 34.1, 35.1, 36.6, 47.8, 48.0, 54.1, 56.7, 66.4, 68.4, 125.1, 125.3, 127.4, 127.5, 127.7, 128.2, 128.3, 128.60, 128.62, 129.2, 129.27, 129.3, 129.88, 129.9, 130.0, 130.3, 130.4, 130.5, 130.7, 130.8, 131.1, 131.2, 131.5, 135.4, 135.7, 135.3, 135.4, 147.9, 148.5.

EXAMPLE 2

A dose response study of induced locomotor stimulation was conducted according to the following procedure. The study was conducted using a 16 or 32 Digiscan locomotor activity testing chambers (40.5×40.5×30.5 cm) housed in sets of two, within sound-attenuating chambers. A panel of infrared beams (16 beams) and corresponding photodetectors were located in the horizontal direction along the sides of each activity chamber. A 15-W incandescent light above each chamber provided dim illumination. Fans provided an 80-dB ambient noise level within the chamber. Separate groups of 8 non-habituated male Swiss-Webster mice (Hsd:ND4, aged 2–3 months) were injected via the intraperitoneal (IP) route with either vehicle (deionized water for Compounds 1–4, carboxymethylcellulose for Compound 6 or methyl cellulose for Compound 7)) or test compound (1, 2.5, 5, 10, 25 or 50 mg/kg for Compound 3; 1, 3, 10 and 30 mg/kg for Compounds 1, 2 and 4; 3, 10, 30 or 100 mg/kg for Compound 6; and 1, 3, 10, 30 and 100 mg/kg for Compound 7). Compounds 1–4 were injected immediately prior to locomotor activity testing. Compound 5 and 6 were injected 20 minutes prior to locomotor activity testing. In all studies, horizontal activity (interruption of photocell beams) was measured for 1 hour within 10 minute periods. Testing was conducted with one mouse per activity chamber.

Figure 13:
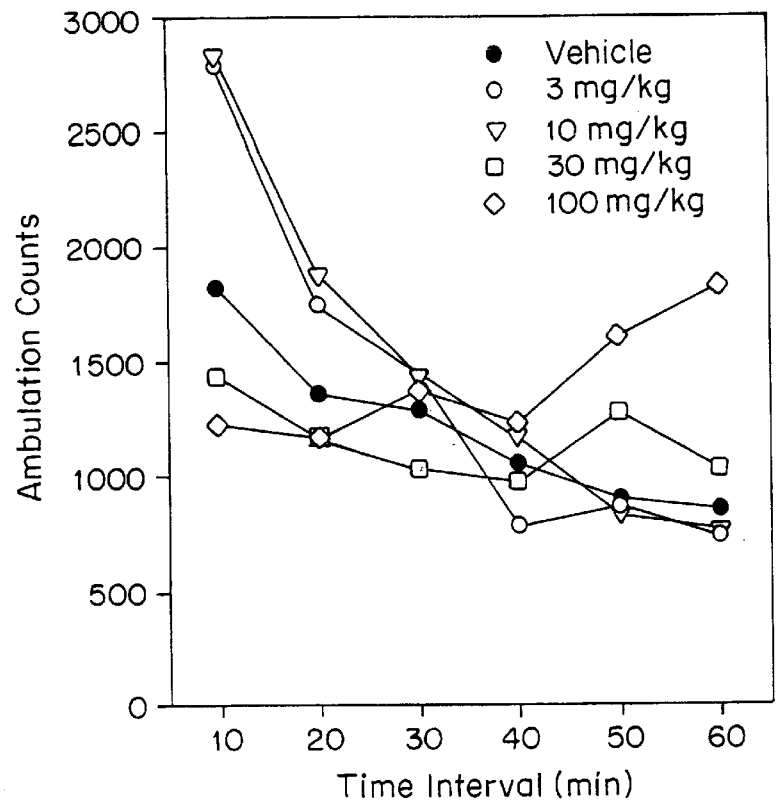
FIG. 13 is a graph showing the number of ambulation counts resulting from the stimulation of locomotor activity in mice over time by the administration of 1) vehicle; 2) 3 mg/kg of Compound 6; 3) 10 mg/kg of Compound 6; 4) 30 mg/kg of Compound 6 and 5) 100 mg/kg of Compound 6.
Figure 14:
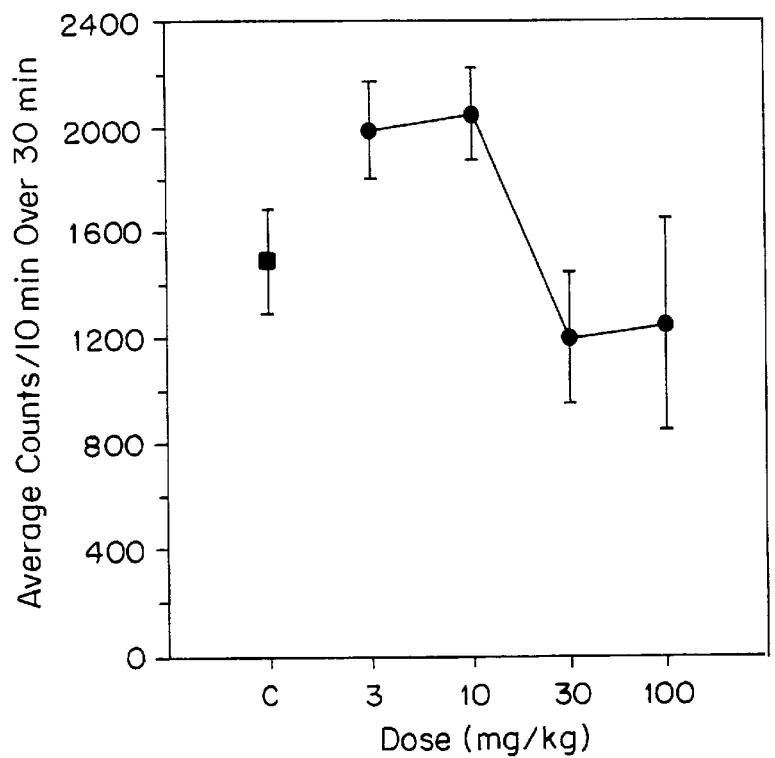
FIG. 14 is a graph showing the average number of ambulation counts/10 minutes over 30 minutes resulting from the stimulation of locomotor activity in mice versus the dosage of Compound 6 administered to the mice.
Figure 15:
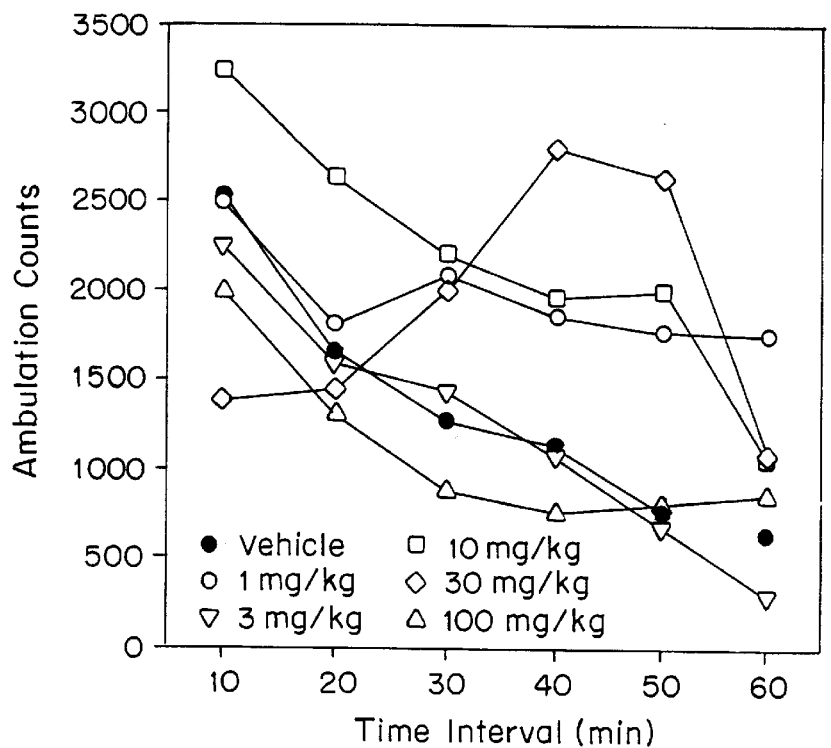
FIG. 15 is a graph showing the number of ambulation counts resulting from the stimulation of locomotor activity in mice over time by the administration of 1) vehicle; 2) 1 mg/kg of Compound 7; 3) 3 mg/kg of Compound 7; 4) 10 mg/kg of Compound 7; 5) 30 mg/kg of Compound 7 and 100 mg/kg of Compound 7.
Figure 16:
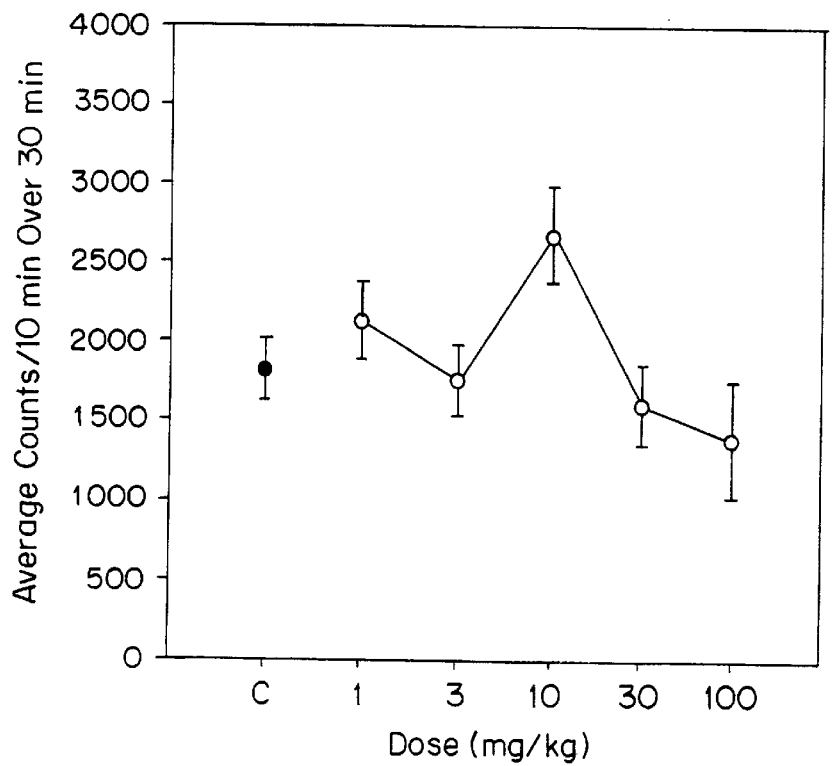
FIG. 16 is a graph showing the average number of ambulation counts/10 minutes over 30 minutes resulting from the stimulation of locomotor activity in mice versus the dosage of Compound 7 administered to the mice.

FIGS. 1, 3, 5 and 7 show average horizontal activity counts/10 minutes as a function of time, immediately following injection of Compound 1, Compound 2, Compound 3 and Compound 4, respectively. FIGS. 13 and 15 show average horizontal activity counts/10 minutes as a function of time, beginning twenty minutes following injection of Compound 6 and Compound 7, respectively. The period 30–60 minutes was selected for analysis of dose-response data. Using TableCurve 2D v2.03 software (Jandel Scientific), the mean average horizontal activity counts/10 minutes for this period were fit to a 3-parameter logistic peak function of log$_{10}$ dose (with the constant set to 1989, the mean of the vehicle-treated group), and the maximum effect estimated from the resulting curve. The ED$_{50}$ for Compounds 1–6 (dose producing ½ maximal stimulant activity) was estimated from a linear regression against log$_{10}$ dose of the ascending portion of the dose-effect curve is shown in Table I below. Compound 7 inhibited locomotor activity; the dose producing ½ maximal inhibitory activity ID$_{50}$ was 184 mg/kg. FIGS. 2, 4, 6, 8, 14 and 16 show average horizontal activity counts/10 minutes over 30 minutes versus the amount administered of Compound 1, Compound 2, Compound 3, Compound 4, Compound 6 and Compound 7, respectively.

TABLE I

Locomotor Activity in the Rat
ED$_{50}$ of Synthesized Compounds AD$_{50}$; of Synthesized Compounds Against 20 mg/kg of Cocaine

| Compound | ED$_{50}$ (mg/kg) | Maximal Effect Relative to Cocaine | AD$_{50}$ (mg/kg) |
|---|---|---|---|
| 4 | 3.90 | 1.07 | not tested |
| 1 | 4.88 | 0.82 | not tested |
| 2 | 5.65 | 0.51 | 13.76 |
| 3 | 10.8 | 0.93 | Not tested |
| 6 | 505.7 | — | 23.6 |

EXAMPLE 3

COMPOUNDS 2, 6 AND 7 BLOCK THE EFFECTS OF COCAINE IN MICE

This interaction study was conducted using 16 Digiscan locomotor activity testing chambers as described in Example 2. Immediately following IP vehicle or Compound 2 injections (1, 3, 10 or 30 mg/kg) groups of 8 non-habituated male Swiss-Webster mice were injected with either vehicle or 20 mg/kg cocaine IP and immediately placed in the Digiscan apparatus for a one hour session. When testing the effects of Compounds 6 and 7, mice were placed in the Digiscan apparatus twenty minutes after the injection of the test compound or vehicle.

Figure 9:
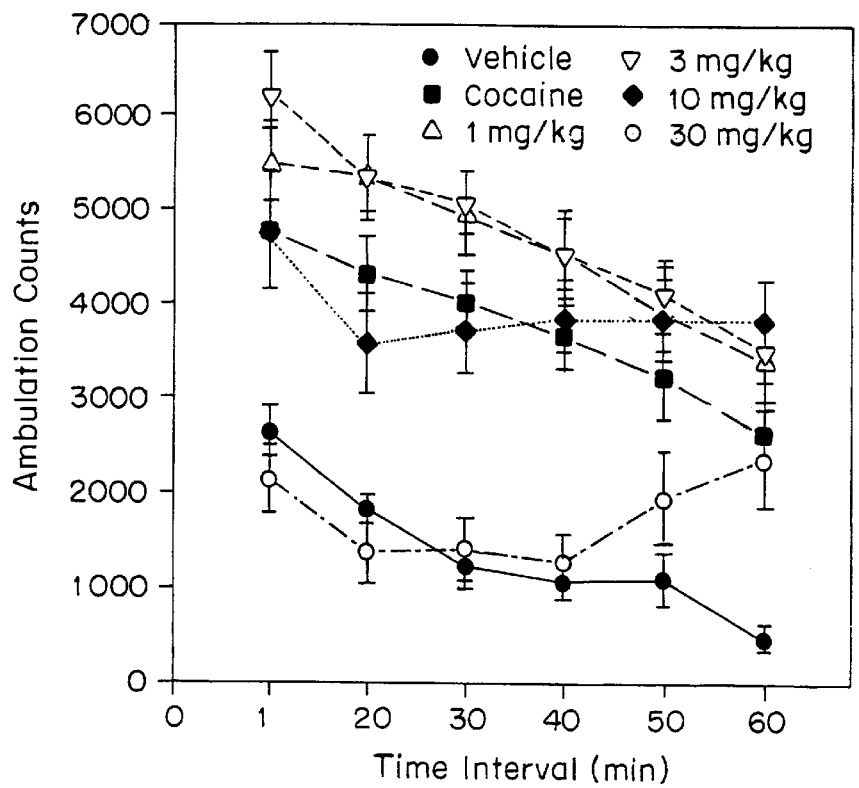
FIG. 9 is a graph showing the number of ambulation counts resulting from the stimulation of locomotor activity in mice over time by the administration of 1) vehicle; 2) cocaine; 3) cocaine and 1 mg/kg of Compound 2; 4) cocaine 3 mg/kg of Compound 2; 5) cocaine and 10 mg/kg of Compound 2; and 6) cocaine and 30 mg/kg of Compound 2.
Figure 10:
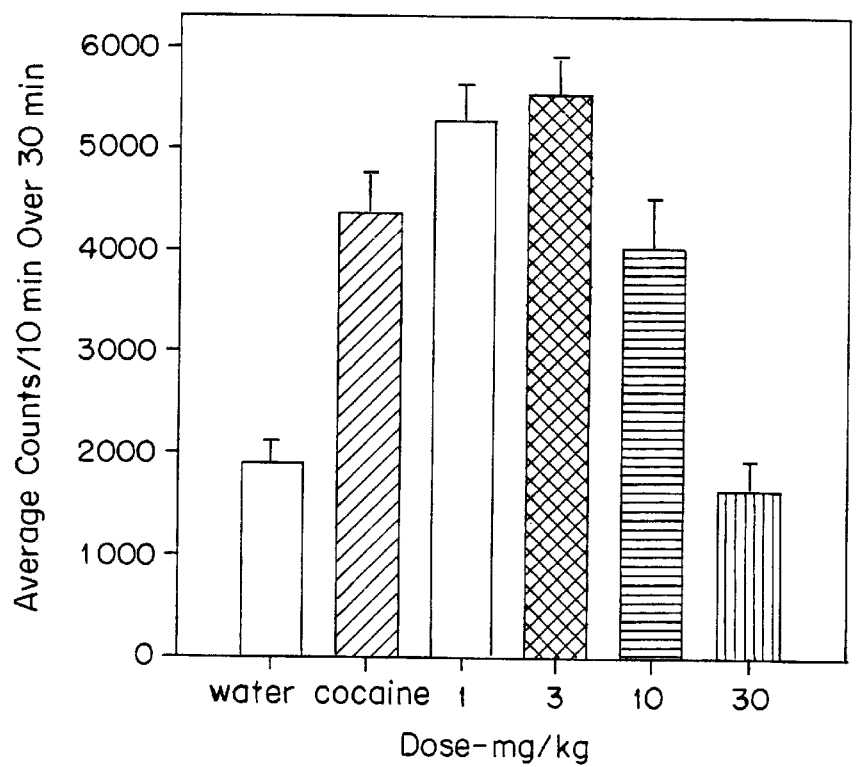
FIG. 10 is a graph showing the average number of ambulation counts/10 minutes over 30 minutes over thirty minutes resulting from the stimulation of locomotor activity in mice induced by the administration of 1) vehicle; 2) cocaine; 3) cocaine and 1 mg/kg of Compound 2; 4) cocaine 3 and mg/kg of Compound 2; 5) cocaine and 10 mg/kg of Compound 2; and 6) cocaine and 30 mg/kg of Compound 2.
Figure 17:
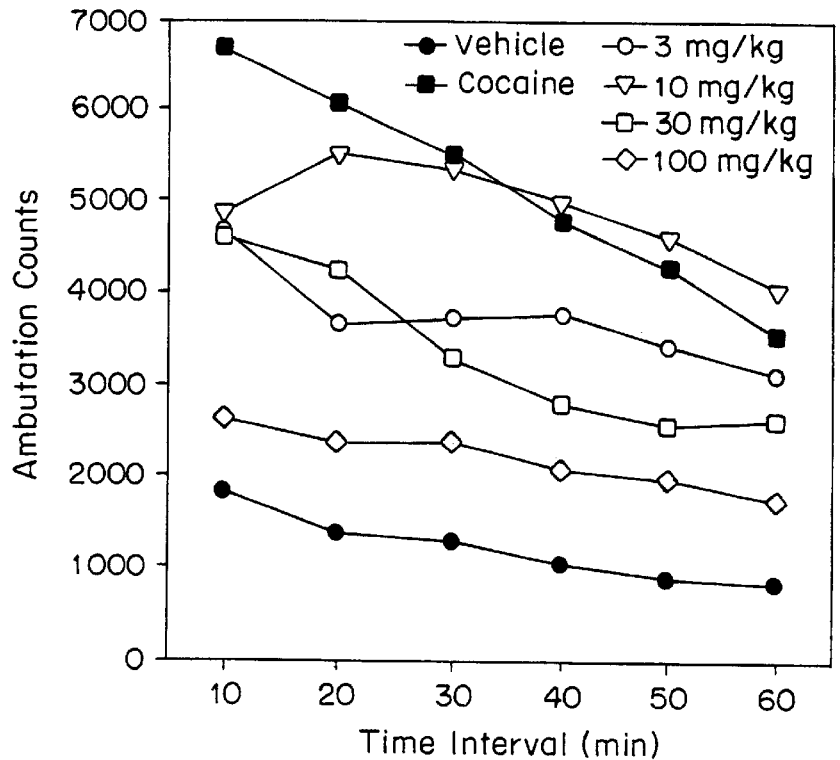
FIG. 17 is a graph showing the number of ambulation counts resulting from the stimulation of locomotor activity in mice over time by the administration of 1) vehicle; 2) cocaine; 3) cocaine and 3 mg/kg of Compound 6; 4) cocaine 10 mg/kg of Compound 6; 5) cocaine and 30 mg/kg of Compound 6; and 6) cocaine and 100 mg/kg of Compound 6.
Figure 18:
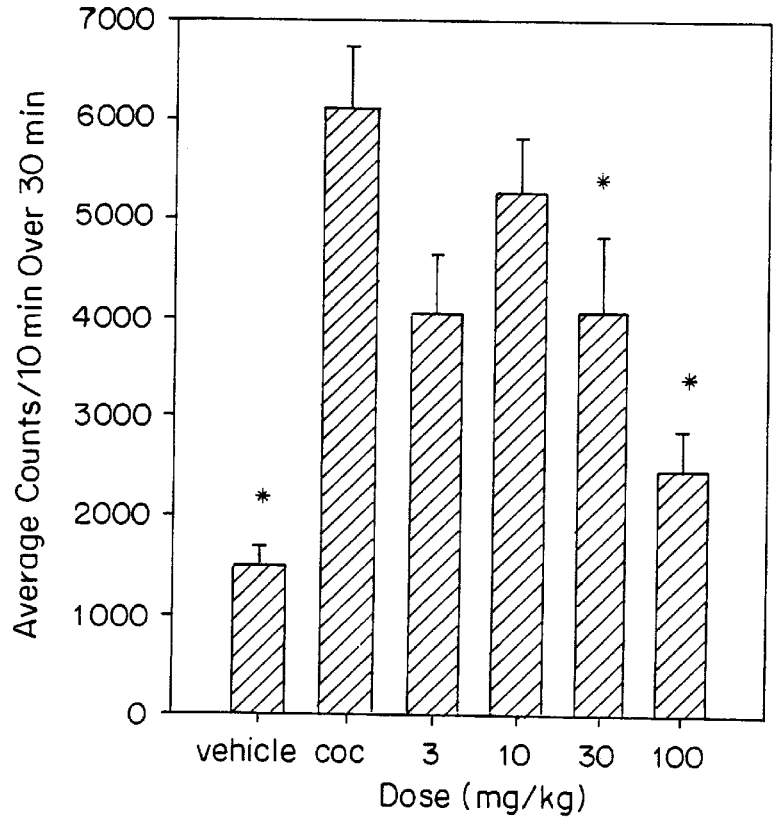
FIG. 18 is a graph showing the average number of ambulation counts/10 minutes over 30 minutes over thirty minutes resulting from the stimulation of locomotor activity in mice induced by the administration of 1) vehicle; 2) cocaine; 3) cocaine and 3 mg/kg of Compound 6; 4) cocaine and 10 mg/kg of Compound 6; 5) cocaine and 30 mg/kg of Compound 6; and 6) cocaine and 100 mg/kg of Compound 6.
Figure 19:
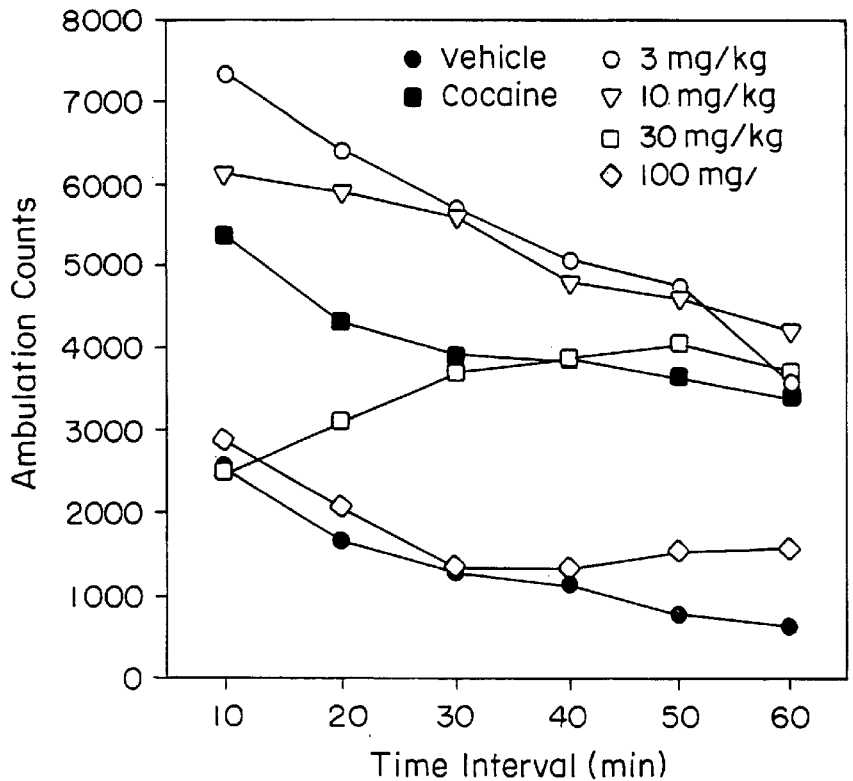
FIG. 19 is a graph showing the number of ambulation counts resulting from the stimulation of locomotor activity in mice over time by the administration of 1) vehicle; 2) cocaine; 3) cocaine and 3 mg/kg of Compound 7; 4) cocaine 10 mg/kg of Compound 7; 5) cocaine and 30 mg/kg of Compound 7; and 6) cocaine and 100 mg/kg of Compound 7.
Figure 20:
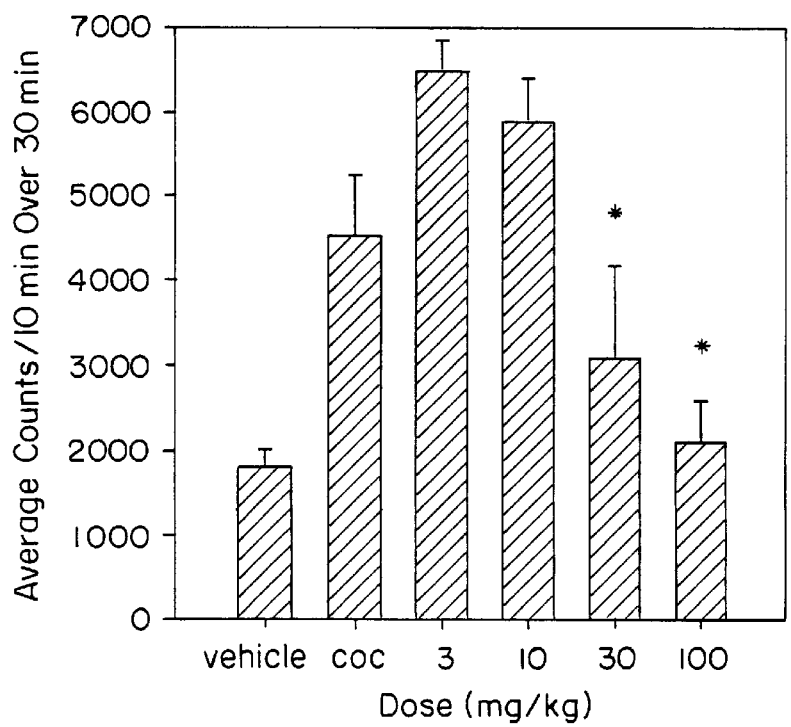
FIG. 20 is a graph showing the average number of ambulation counts/10 minutes over 30 minutes over thirty minutes resulting from the stimulation of locomotor activity in mice induced by the administration of 1) vehicle; 2) cocaine; 3) cocaine and 3 mg/kg of Compound 7; 4) cocaine and 10 mg/kg of Compound 7; 5) cocaine and 30 mg/kg of Compound 7; and 6) cocaine and 100 mg/kg of Compound 7.

FIGS. 9, 17 and 19 show average horizontal activity counts for the different treatment groups as a function of time. The period of 0–30 minutes was selected for analysis of dose-response data because this is the time period in which cocaine produces maximal effects. FIGS. 10, 18 and 20 show average horizontal activity counts/10 min for different treatment groups as a function of dose. In FIG. 10, the bar above "water" represents the effect of vehicle immediately following saline injection; the bar above "cocaine" represents the effect of the 20 mg/kg cocaine immediately following the vehicle injection; The bars above "1", "3", "10", and "30" represent the effects of Compound 2 at the designated doses following the cocaine injection. In FIGS. 18 and 20, the bar above "vehicle" represents the effect of vehicle twenty minutes prior to saline injection; the bar above "coc" represents the effect of vehicle twenty minutes prior to 20 mg/kg cocaine injection; and the bars above "1", "3", "10", "30" and "100" represent the effects of Compound 6 or Compound 7 at the designated doses twenty minutes prior to 20 mg/kg cocaine injection.

Compounds 2, 6 and 7 antagonized the stimulant effect of cocaine and the AD$_{50}$ (dose attenuating cocaine-induced stimulation by 50%) was calculated to be 13.76 mg/kg for Compound 2 (3–30 mg/kg Compound 2), 23.6 6 mg/kg Compound 6 (3–100 mg/kg dose range) and 42.5 mg/kg for Compound 7 (3–100 mg/kg dose range). The ordinate value for the AD$_{50}$ was calculated using the mean of the vehicle plus 20 mg/kg cocaine (cocaine) group as the maximum value.

A one-way analysis of variance conducted on log$_{10}$ horizontal activity counts for the selected time period indicated a significant overall effect for the treatment groups; $F(4, 35)=15.92$, $p>0.05$ for Compound 2; $F(5,42)=7.95$ $p<0.5$ for Compound 6; and $F((5,42)=8.96$ $p<0.5)$. Planned comparisons (a priori contrast) against the cocaine group showed significant differences for vehicle and 30 mg/kg Compound 2; and for vehicle and 30 and 100 mg/kg Compound 6 and Compound 7. All $ps<0.05$ are denoted in FIGS. 10, 18 and 20 with an asterisk.

EXAMPLE 4

INHIBITION OF BINDING OF DOPAMINE TO THE DOPAMINE TRANSPORTER AND INHIBITION OF DOPAMINE REUPTAKE BY COMPOUND 1 AND COMPOUND 5

The inhibition of binding of dopamine to the dopamine transporter and inhibition of dopamine reuptake was determined for Compounds 1 and 5 according to the methods disclosed in Deutsch et al., *J. Med. Chem.* 39:1201 (1996). The results are shown in Table II below.

TABLE II

Binding and Dopamine Transporter ($IC_{50}$; nM) and Inhibition of Dopamine Reuptake ($IC_{50}$; nM)

|  | Binding | DA Uptake | Uptake/Binding |
|---|---|---|---|
| Cocaine | 300 ± 40 | 250 ± 50 | 0.83 |
| Compound 5 | 9.5 | 9.8 | 1.03 |
| Compound 1 | 47 | 56 | 1.19 |

EXAMPLE 5

COMPOUND 1 SHOWS LONG-LASTING LOCOMOTOR RESPONSE IN PRIMATES

Figure 11:
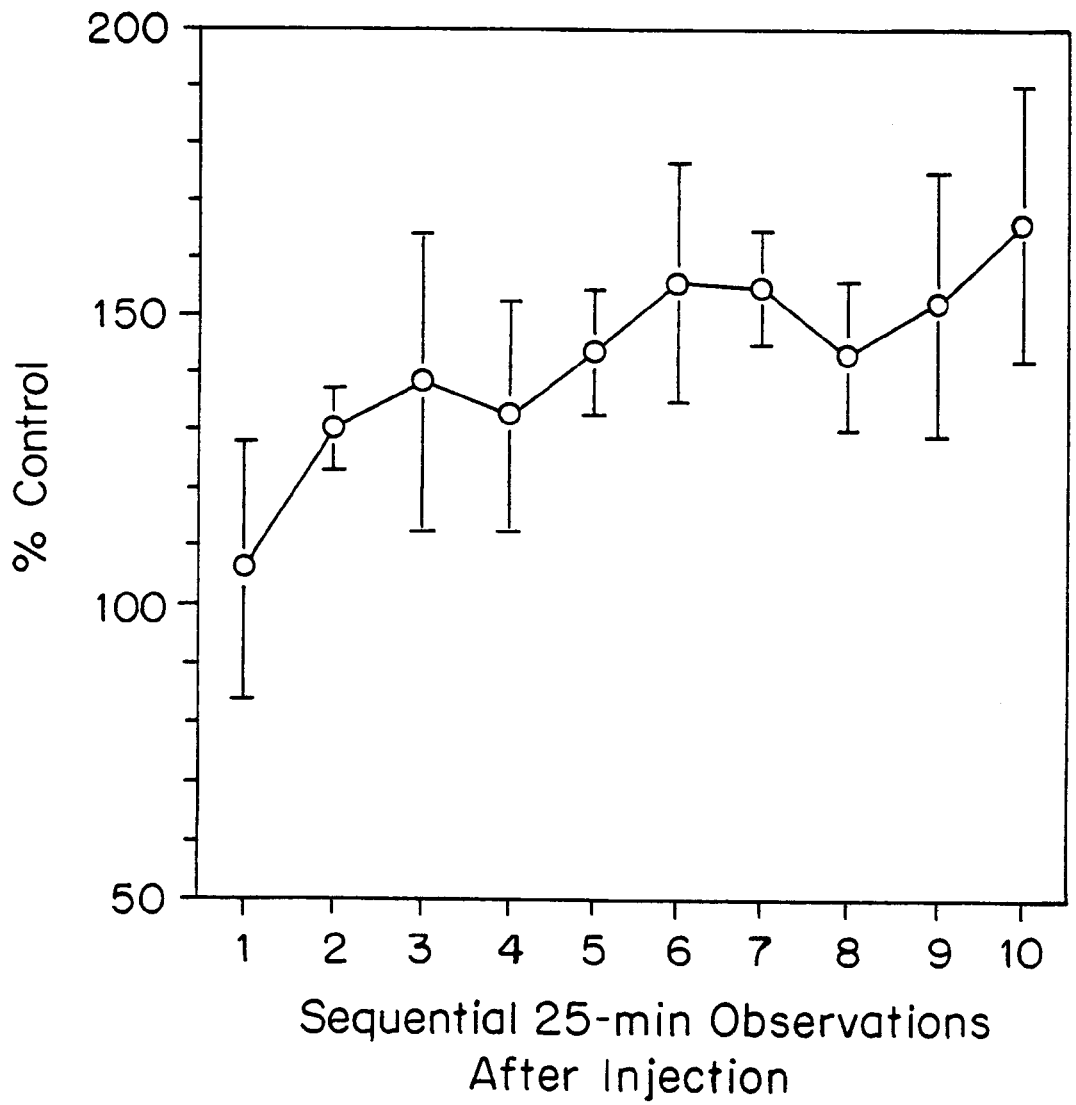
FIG. 11 is a graph showing the locomotor activity in a primate model at 25 minute intervals following the administration of a single dose of 1.0 mg/kg of Compound 1.
Figure 12:
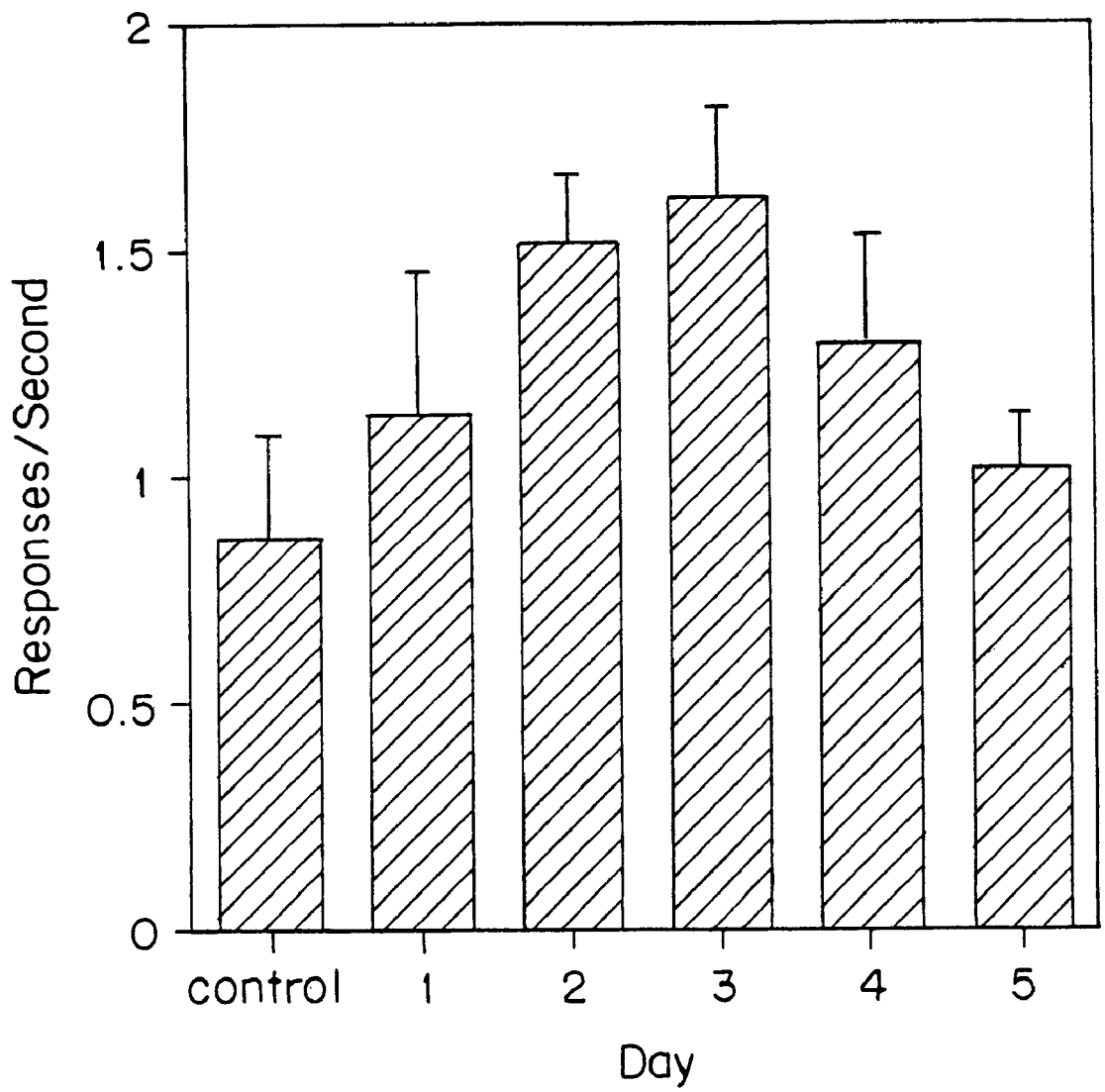
FIG. 12 is a graph showing the degree of locomotor response in a primate model over a five day period following the administration of a single dose of 1.0 mg/kg of Compound 1.

Compound 1 was tested for its ability to induce a locomotor response in primates according to procedures disclosed in Rosenzweig-Lipson et al., *Psychopharmacology* 107:186 (1992). Three squirrel monkeys were administered 1.0 mg/kg of Compound 1. The response was measured over 25 minute intervals, as shown in FIG. 11. As observed in mice, Compound 1 induced a slow onset locomotor response. As shown in FIG. 12, the locomotor response in primates peaked at three days. The results for each monkey are shown below in Table III and is presented as the responses per second on each day of the test. Controls were established by testing each monkey prior to administering Compound 1. As can be seen, the increase in response rate lasted for 5–7 days. The experiment was repeated by administering 0.3 mg/kg of Compound 5 to three squirrel monkeys. The results for each monkey are also shown in Table III. As can be seen, the increase in response rate lasted only from about two to four days.

TABLE III

Number of Responses/Second in Squirrel Monkeys Administered 0.3 mg/kg of Compound 5

| Days After Administration | Monkey 1 | Monkey 2 | Monkey 3 |
|---|---|---|---|
| Control | 0.74 | 0.72 | 0.92 |
| Day 1 | 1.29 | 0.87 | 1.11 |
| Day 2 | 0.99 | 1.18 | 1.28 |
| Day 3 | 0.75 | 0.88 | 1.13 |
| Day 4 | 0.79 | 0.74 | 1.01 |

Number of Responses/Second in Squirrel Monkeys Administered 1.0 mg/kg of Compound 1

| After Administration | Monkey 4 | Monkey 5 | Monkey 6 |
|---|---|---|---|
| Control | 1.15 | 0.51 | 0.93 |
| Day 1 | 1.63 | 0.76 | 1.01 |
| Day 2 | 1.72 | 1.50 | 1.31 |
| Day 3 | 1.92 | 1.51 | 1.40 |
| Day 4 | 1.06 | 1.01 | 1.16 |
| Day 5 | 1.05 | 0.82 | 1.14 |
| Day 6 |  | 0.62 |  |
| Day 7 |  | 0.60 |  |

EXAMPLE 6

STIMULATION OF LOCOMOTOR ACTIVITY IN MICE BY COMPOUND 2 LASTS UP TO SEVEN HOURS

COCAINE ALONE STUDY

A dose response study of induced locomotor stimulation was conducted according to the following procedure. The study was conducted using 16 Digiscan locomotor activity testing chambers (40.5×40.5×30.5 cm) housed in sets of two, within sound-attenuating chambers. A panel of infrared beams (16 beams) and corresponding photodetectors were located in the horizontal direction along the sides of each activity chamber. A 7.5-W incandescent light above each chamber provided dim illumination. Fans provided an 80-dB ambient noise level within the chamber. Separate groups of 8 non-habituated male Swiss-Webster mice (Hsd:ND4, aged 2–3 months) were injected via the intraperitoneal (IP) route with either vehicle (0.9% saline) or test compound (5, 10, 20 or 40 mg/kg), immediately prior to locomotor activity testing. In all studies, horizontal activity (interruption of photocell beams) was measured for 8 hours within 10 minute periods, beginning at 0880 hours) two hours after lights on). Testing was conducted with one mouse per activity chamber.

Figure 21:
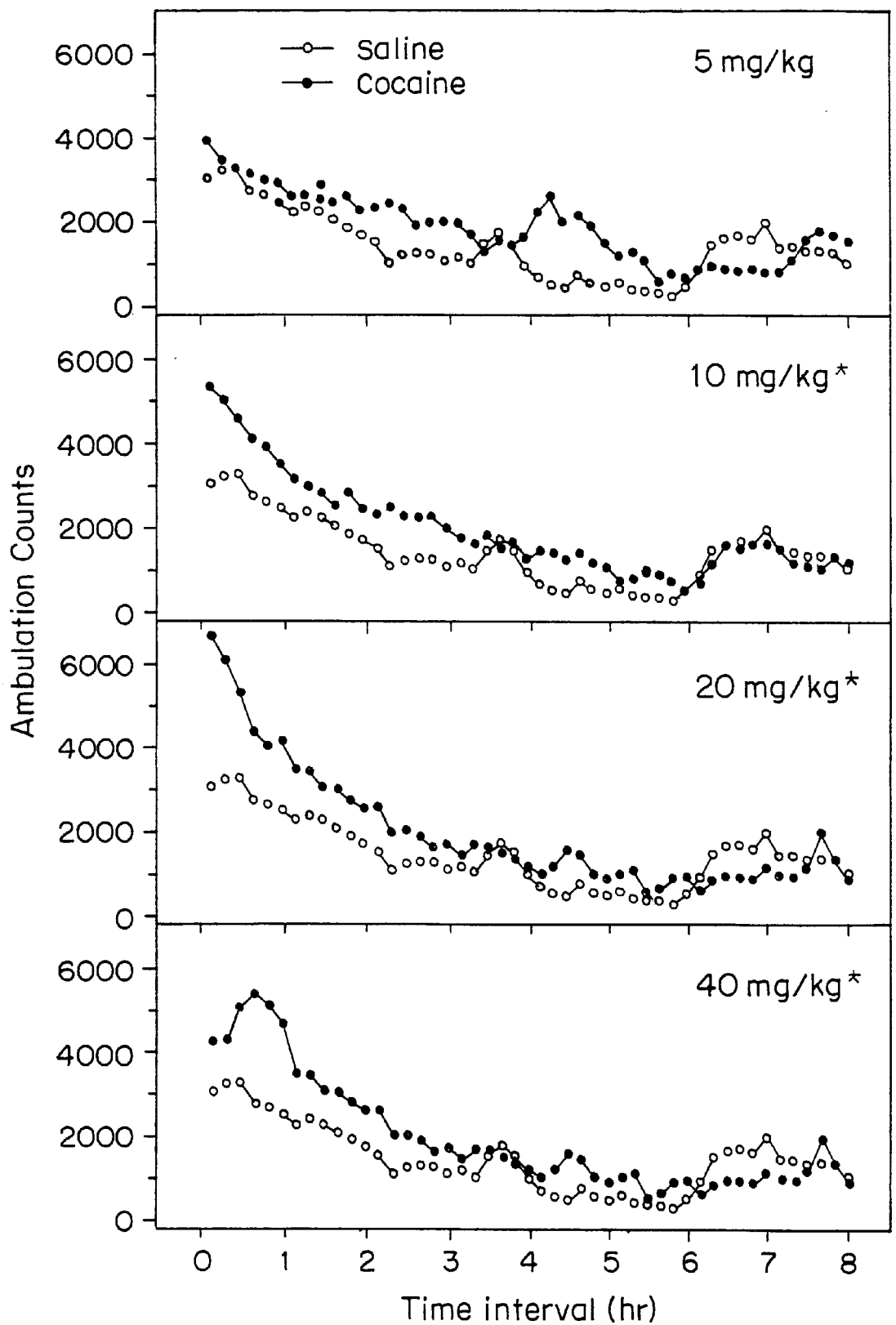
FIG. 21 is a graph showing the effect on mice of 1) 5 mg/kg, 2) 10 mg/kg, 3) 20 mg/kg and 4) 40 mg/kg of cocaine compared with saline on horizontal activity counts/10 minute over an eight hour session.

FIG. 21 shows average horizontal activity counts/10 min as a function of time (0–8 hr) and dose of cocaine (top to bottom panels). Treatment with cocaine resulted in time-dependent stimulation of locomotor activity in doses from 10 to 40 mg/kg. Stimulant effects of 10, 20 and 40 mg/kg occurred within 10 minutes following injection and lasted up to 3 hours. Maximal stimulant effects were evident during the first 30 minutes following 20 mg/kg cocaine, and this period was selected for analysis of dose-response data. Using TableCurve 2D v2.03 software (Jandel Scientific), the mean average horizontal activity counts for this 30-min period were fit to a 3-parameter logistic peak function of $log_{10}$ dose (with the constant set to 3172, the mean of the saline-treated group), and the maximum was estimated from the resulting curve (maximum=6059 counts/10 min at 18.3 mg/kg). The $ED_{50}$ (dose producing one half maximal stimulant activity) was estimated at 8.8 mg/kg from a linear regression against $log_{10}$ dose of the ascending portion of the dose-effect curve (5–20 mg/kg cocaine).

A two-way analysis of variance conducted on horizontal activity counts/10 min indicated a significant interaction of Treatment with 10-Minute Periods, as well as a main effect of 10-Minute Periods ($ps<0.001$). The main effect of Treatment was not significant in the two-way analysis, $F(4,35)=2.2$, $p=0.089$. A one-way analysis of variance conducted on $\log_{10}$ horizontal activity counts for the 0–30 min time period (maximal stimulant effect) indicated a significant effect of Treatment $F(4,35)=9.1$, $p<0.001$, and planned comparisons (a priori contrast) against the vehicle group showed a significant difference for 10, 20 and 40 mg/kg (all $ps<0.05$ denoted on FIG. 21 with an asterisk).

COMPOUND 2 ALONE STUDY

A time course study of Compound 2-induced locomotor stimulation was conducted under the same conditions as outlined above for the cocaine alone study described above. Separate groups of eight mice were injected with either vehicle (deionized water) or Compound 2 (1, 3, 10 pr 30 mg/kg) immediately prior to locomotor activity testing.

Figure 22:
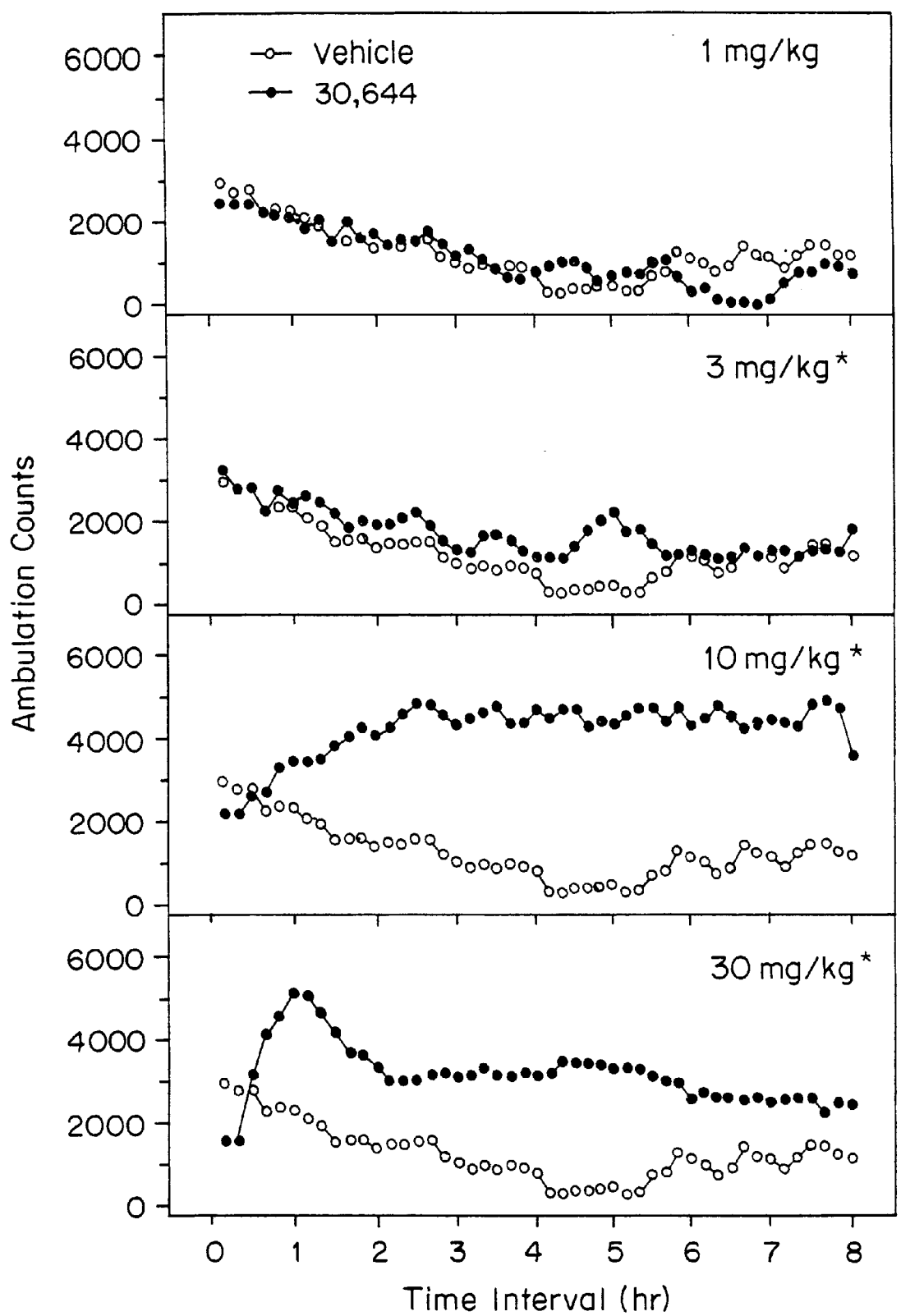
FIG. 22 is a graph showing the effect on mice of 1) 1 mg/kg, 2) 3 mg,/kg, 3) 10 mg/kg and 4) 30 mg/kg of Compound 2 compared with saline on horizontal activity counts/10 minute over an eight hour session.
Figure 23A:
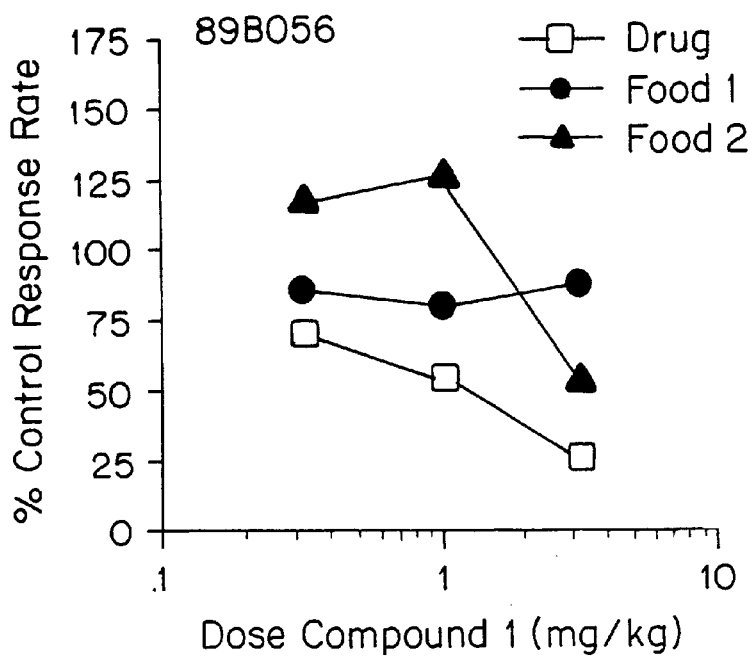
FIG. 23A through 23D are graphs showing the effects of Compound 1 on responding maintained by cocaine and food in monkeys 89BO56, WH8, J3A and 89B013. The graph shows the dose of Compound 1 in mg/kg versus the percent control rates of responding maintained by cocaine during the drug component (Drug) and by food during the first food component (Food 1) and the second food component (Food 2) (see Example 7).
Figure 23B:
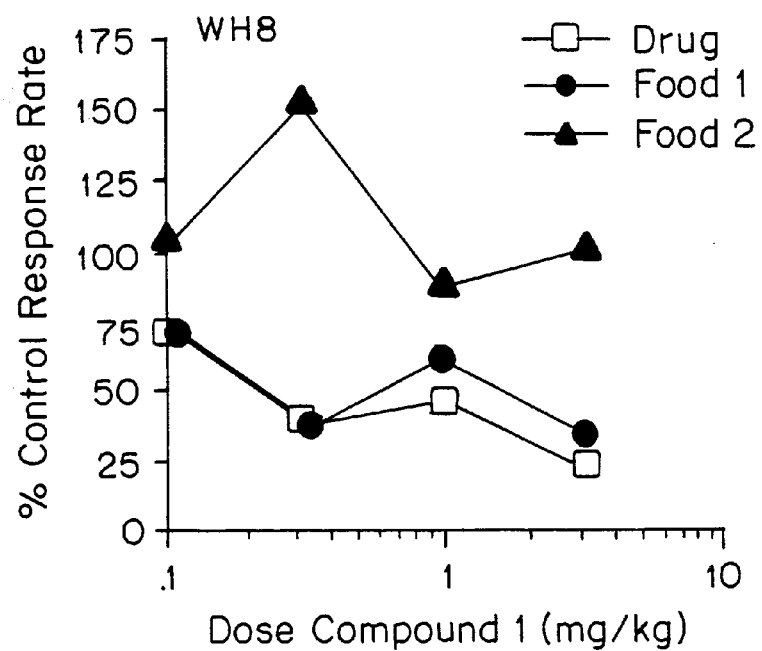
Figure 23C:
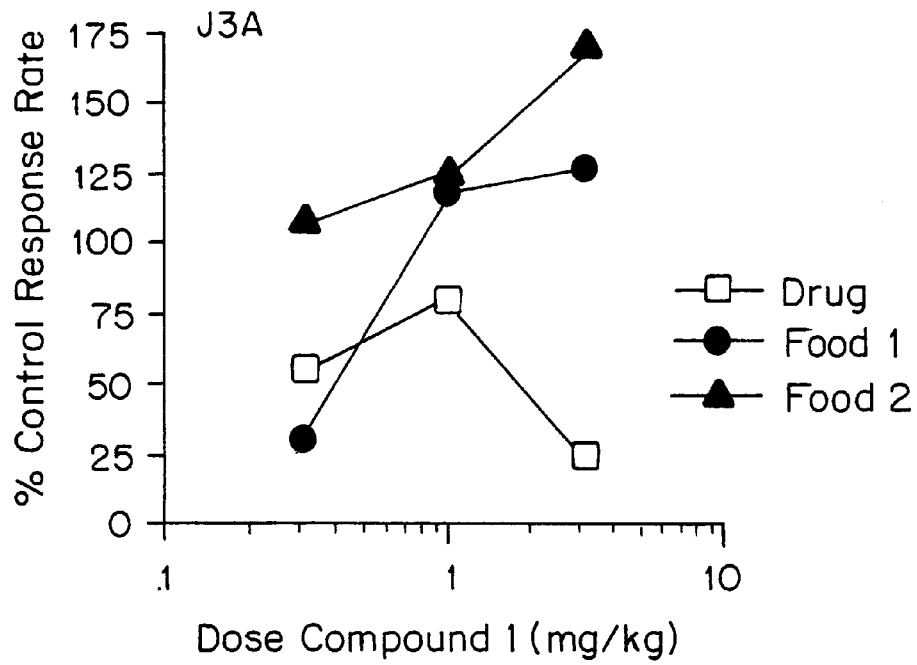
Figure 23D:
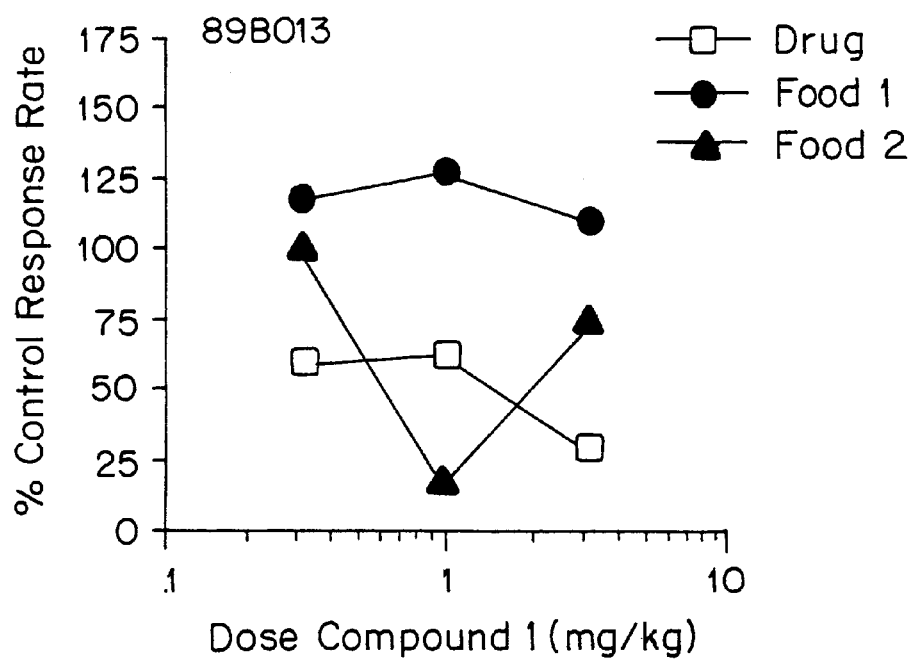

FIG. 22 shows average horizontal activity counts/10 min as a function of time (0–8 hr) and dose of Compound 2 (top to bottom panels). Treatment with Compound 2 resulted in time-dependent stimulation of locomotor activity in doses from 3 to 30 mg/kg. Stimulant effects occurred within 40 to 70 minutes following injection and lasted 4 to ≧7 hours. The time period 280–310 min was selected for analysis of dose-response data because this was the time period in which maximal stimulant effects first appeared as a function of dose. Using TableCurve 2D v2.03 software (Jandel Scientific), the mean average horizontal activity counts/10 min for this period were fit to a 3-parameter logistic peak function of $\log_{10}$ dose (with the constant set to 399, the mean of the vehicle-treated group), and the maximum effect estimated from the resulting curve (maximum=4581 counts/10 min at 12.9 mg/kg). The $ED_{50}$ (dose producing one half maximal stimulant activity) was estimated at 3.3 mg/kg from a linear regression against $\log_{10}$ dose of the ascending portion of the dose-effect curve (1 to 10 mg/kg 30,644). The maximal effect/cocaine maximal effect ratio (ME/CME) was equal to 1.4 based upon the cocaine dose-effect data determined described above.

A two-way analysis of variance conducted on horizontal activity counts/10 min indicated significant effects of Treatment $F(4,35)=21.5$, $p<0.001$, 10-Minute Periods $F(47, 1645)=5.9$, $p<0.001$, and the interaction of those factors $F(188,1645)=4.5$, $p<0.001$. A one-way analysis of variance conducted on $\log_{10}$ horizontal activity counts for the 280–310 min time period (maximal stimulant effect) indicated a significant effect of Treatment $F(4,35)=21.3$, $p<0.001$, and planned comparisons (a priori contrast) against the vehicle group showed a significant difference for 3, 10 and 30 mg/kg (all $ps<0.05$ denoted on FIG. 22 with an asterisk).

EXAMPLE 7

COMPOUND 1 PRODUCES A DOSE-DEPENDENT DECREASE IN COCAINE SELF-ADMINISTRATION IN RHESUS MONKEYS

Subjects

The subjects were four male rhesus monkeys (*Macaca mulatta*). Each monkey was maintained on a diet of 3–4 monkey biscuits (Purina Monkey Chow Jumbo #5037) and one piece of fresh fruit per day in addition to fruit-flavored pellets delivered during operant sessions (see below). Water was freely available at all times. The monkeys were housed in a humidity and temperature controlled room with a 12 hr light-dark cycle (lights on from 7 a.m. to 7 p.m.).

Monkeys were surgically implanted with double-lumen Silicone rubber catheters (inside diameter 0.7 mm; outside diameter 2.0 mm) to facilitate concurrent delivery of cocaine and treatment compounds. Catheters were implanted in the jugular or femoral vein, and the catheters exited in the midscapular region. All surgical procedures were performed under aseptic conditions. Monkeys were initially sedated with ketamine (5 mg/kg, s.c.), and anesthesia was induced with sodium thiopental (10 mg/kg, i.v.). In addition, monkeys were treated with 0.05 mg/kg atropine to reduce salivation. Following insertion of a tracheal tube, anesthesia was maintained with isoflurane (1–1.5% in oxygen). After surgery, monkeys were administered aspirin or acetaminophen (80–160 mg/day: p.o.) for 3 days. The antibiotic Procaine Penicillin G (300,000 units/day, i.m.) was administered every day for 5 days. The i.v. catheter was protected by a tether system consisting of a custom-fitted nylon vest connected to a flexible stainless steel cable and fluid swivel (Lomir Biomedical; Malone, N.Y.). This flexible tether system permitted monkeys to move freely. Catheter patency was periodically evaluated by i.v. administration of the short-acting barbiturate methohexital (3 mg/kg i.v.) or ketamine (2–3 mg/kg i.v.). The catheter was considered patent if i.v. administration of methohexital or ketamine produced loss of muscle tone within 10 seconds after its administration.

Animal maintenance and research are conducted in accordance with the guidelines provided by the NIH Committee on Laboratory Animal Resources. The facility is licensed by the United States Department of Agriculture, and protocols are approved by the Institutional Animal Care and Use Committee. The health of the monkeys is periodically monitored by consulting veterinarians. Monkeys have visual, auditory and olfactory communications with other monkeys, and operant procedures provide an opportunity for environmental manipulation and enrichment.

Apparatus

Each monkey was housed individually in a well-ventilated stainless steel chamber(64×64×79 cm). The home cages of all monkeys were modified to include an operant panel (28×28 cm) mounted on the front wall. Three square translucent response keys (6.4×6.4 cm) were arranged 2.54 cm apart in a horizontal row 3.2 cm from the top of the operant panel. Each key could be transilluminated by red or green stimulus lights (Superbright LED's). The operant panel also supported an externally-mounted pellet dispenser (Gerbrands, Model G5210) that delivered 1 gm fruit-flavored food pellets (Precision Primate Pellets Formula L/I Banana Flavor or Precision Purified Pellets Formula L/P Grape Flavor, P. J. Noyes Co., Lancaster, N.H.) to a food receptacle mounted on the cage beneath the operant response panel. Two syringe pumps (Model B5P-1E, Braintree Scientific, Braintree, Mass.; or Model 980210, Harvard Apparatus, South Natick, Mass.) were mounted above each cage for delivery of saline or drug solutions through the intravenous catheters. Operation of the operant panels and data collection were controlled by a MED-PC interface and IBM compatible computer programmed in MED-STATE Notation (MEDAssociates, Inc., East Fairfield, Vt.).

Training

Food and i.v. drug or saline injections were available during three alternating components: a 5-min food component, a 100-min drug component, and a second 5-min food component. Both food and i.v. injections were available under a FR30 schedule of reinforcement. During the two food components, the response key was transilluminated red. During the drug component, the response key was transilluminated green. Following the delivery of each food pellet or drug injection, there was a 10 sec timeout period, during which the stimulus light illuminating the center response key was turned off and responding had no scheduled consequences. The food and drug components were separated by 5-min timeout periods when the response key was dark, and responding had no scheduled consequences. The entire food/drug/food session lasted 120 min and was conducted daily from 3–5 p.m.

In addition to the food/drug/food session described above, monkeys were also given the opportunity to self-administer additional food pellets during supplementary food sessions running from 7–8 p.m. and 6–7 a.m. During these sessions, food was available under a FR30/Timeout 10 sec schedule, and a maximum of 25 pellets per session could be earned. These food sessions provided enrichment opportunities for the monkeys and behavioral information relevant for the evaluation of prolonged treatment drug effects.

During training, the solution available for self-administration during the drug component was alternated between 0.032 mg/kg/inj cocaine (the maintenance dose of cocaine) and saline. Each period of cocaine or saline availability usually lasted from 3 to 10 days. Monkeys were trained until they met the following criteria for stable cocaine self-administration: 1) three consecutive days during which the response rate during the drug component of each session differed by no more than 20% from the mean drug component response rate and there was no upward or downward trend; and 2) rapid saline extinction as indicated by a decrease in drug component response rates on the first day of saline substitution.

Evaluation of Compound 1

The effects of Compound 1 on cocaine and food self-administration were evaluated using the pretreatment test procedure. In this procedure, Compound 1 was administered i.m. 30 min prior to a test session during which a test unit dose of cocaine was available during the drug component of the session. During initial studies, the pretreatment dose of Compound 1 was varied from 0.1 to 3.2 mg/kg, and the unit dose of cocaine was maintained at either 0.0032 mg/kg (monkeys 89B056, 89B013 and J3A) or 0.01 mg/kg/inj (monkey WH8). These unit doses of cocaine were individually selected from the peak of each monkey's cocaine dose-effect curve. During subsequent studies, the dose of Compound 1 was held constant at 3.2 mg/kg, and the unit dose of cocaine was varied to allow determination of the effects of 3.2 mg/kg Compound 1 on the complete cocaine dose-effect curve. This second series of studies was conducted on monkeys 89B056, 89B013 and J3A. Each combination of a dose of Compound 1 and a test unit dose of cocaine was examined for one test session.

At the conclusion of each pretreatment test, the training conditions (availability of saline or the maintenance dose of cocaine) were reinstated. Test sessions were conducted on Tuesdays and Fridays. Either saline or the maintenance dose of cocaine was available for the remaining sessions during the week. In addition, test days were occasionally omitted to allow several days of saline substitution.

Data Analysis

The dependent variables were the response rates during each food and drug component. The response rate was calculated as [total number of responses/(component duration—Σ timeouts)]. Control response rates for each food and drug component during availability of each unit dose of cocaine were defined as the response rate obtained when that unit dose of cocaine was available and no pretreatment was administered.

Drugs

Cocaine hydrochloride was dissolved in saline. A stock solution of 10 mg/ml Compound 1 was prepared using a vehicle of 50% propylene glycol and 50% distilled water, and dilutions were made with distilled water. Aseptic precautions were taken in every phase of cocaine solution preparation and dispensing. Cocaine solutions were filter-sterilized using an 0.22 micron Millipore Filter and stored in sterile, pyrogen-free vials. Sterility of the entire fluid path for drug solutions was maintained throughout the study. Each unit dose of cocaine was delivered i.v. in an injection volume of 0.1 ml. Doses of Compound 1 were delivered i.m. in a volume of 0.2–3.0 ml.

RESULTS

Table IV shows the control rates of cocaine and food-maintained responding during availability of a unit dose of cocaine selected from the peak of each monkey's cocaine dose-effect curve (0.0032 mg/kg/inj in monkeys 89B013, 89B056 and J3A and 0.01 mg/kg/inj cocaine in monkey WH8). FIG. 23 shows the effects of Compound 1 (0.1–3.2 mg/kg) on these control rates of cocaine and food-maintained responding. Compound 1 produced a dose-dependent decrease in rates of cocaine self-administration; however, the dose-effect curve for Compound 1 was relatively shallow across the dose-range tested. In general, doses of 0.1–1.0 mg/kg Compound 1 decreased rates of cocaine self-administration to 50–75% of control levels, whereas a higher dose of 3.2 mg/kg Compound 1 decreased rates of cocaine self-administration to approximately 25% of control levels. The effects of Compound 1 or rates of food-maintained responding during the first and second components were variable. However, relative to its effects on cocaine self-administration, Compound 1 usually produced either smaller decreases in rates of food-maintained responding or increased rates of food-maintained responding.

TABLE IV

Control rates of responding (responses/sec) maintained by cocaine and food during availability of a unit dose of cocaine located at the peak of each monkey's cocaine dose-effect curve. The unit dose of cocaine was 0.0032 mg/kg/inj for monkeys 89B013, 89B056 and J3A and 0.01 mg/kg/inj for monkey WH8.

| Monkey | Component | | |
|---|---|---|---|
| | Drug | Food #1 | Food #2 |
| 89B013 | 0.51 | 3.48 | 4.7 |
| 89B056 | 0.79 | 7.78 | 6.05 |
| J3A | 0.57 | 1.8 | 1.42 |
| WH8 | 0.45 | 2.06 | 1.68 |

Figure 24A:
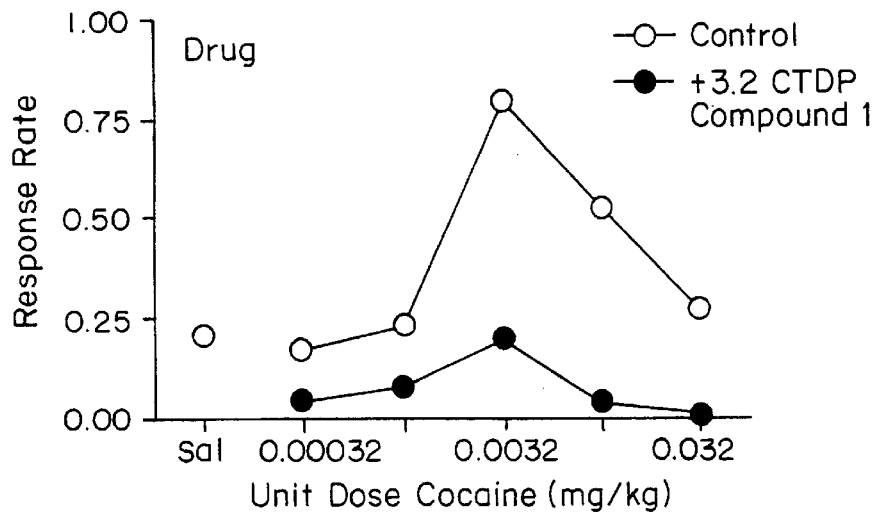
FIG. 24A through 24C are graphs showing the effects of Compound 1 on the complete cocaine dose-effect curve in monkey 89B056. The graph shows the unit dose cocaine available during the drug component in mg/kg/injection versus the response rate in responses/sec. Panels show data from the drug component (top panel), first food component (middle panel) and second food component (bottom panel) (see Example 7).
Figure 24B:
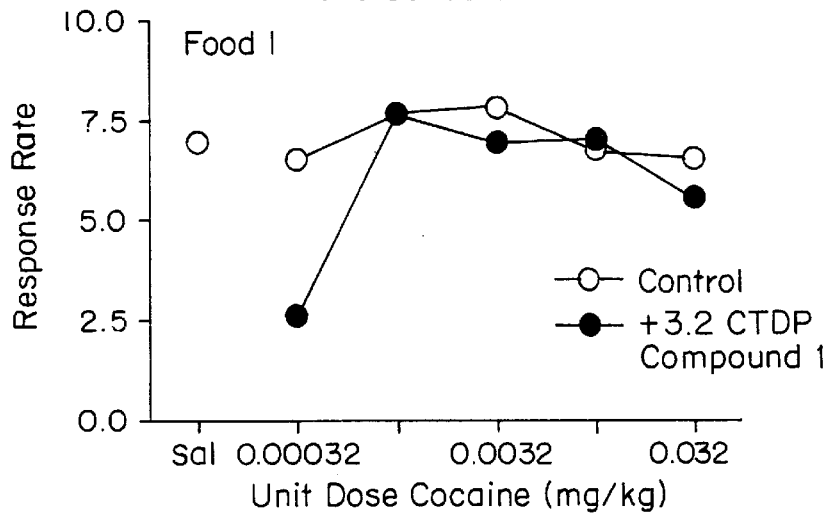
Figure 24C:
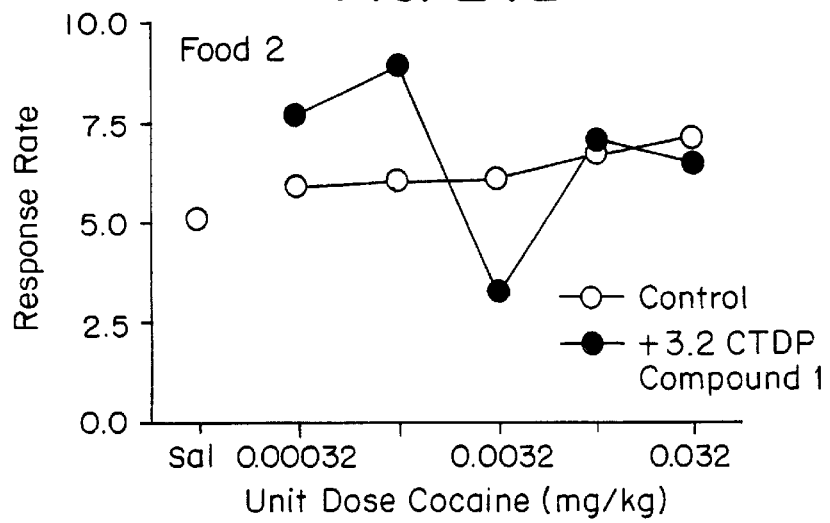
Figure 25A:
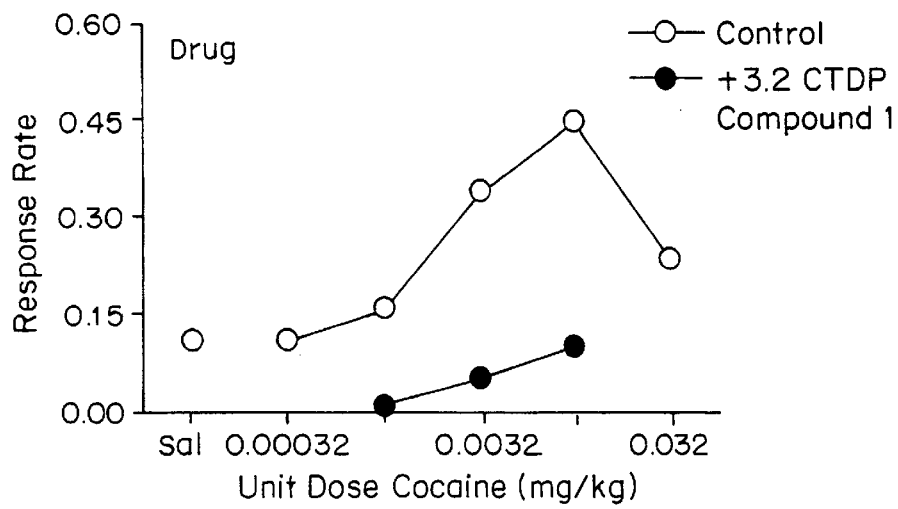
FIG. 25A through 25C are graphs showing the effects of Compound 1 on the complete cocaine dose-effect curve in monkey WH8. The graph shows the unit dose cocaine available during the drug component in mg/kg/injection versus the response rate in responses/sec. Panels show data from the drug component (top panel), first food component (middle panel) and second food component (bottom panel) (see Example 7).
Figure 25B:
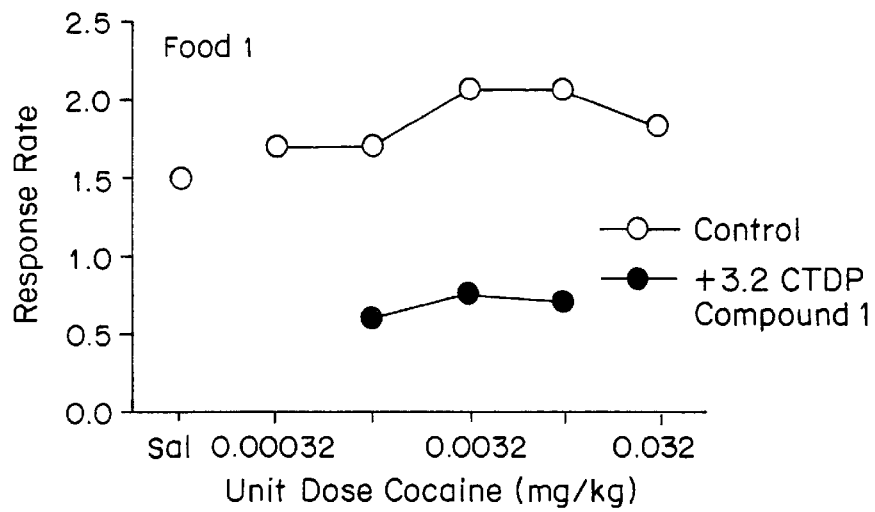
Figure 25C:
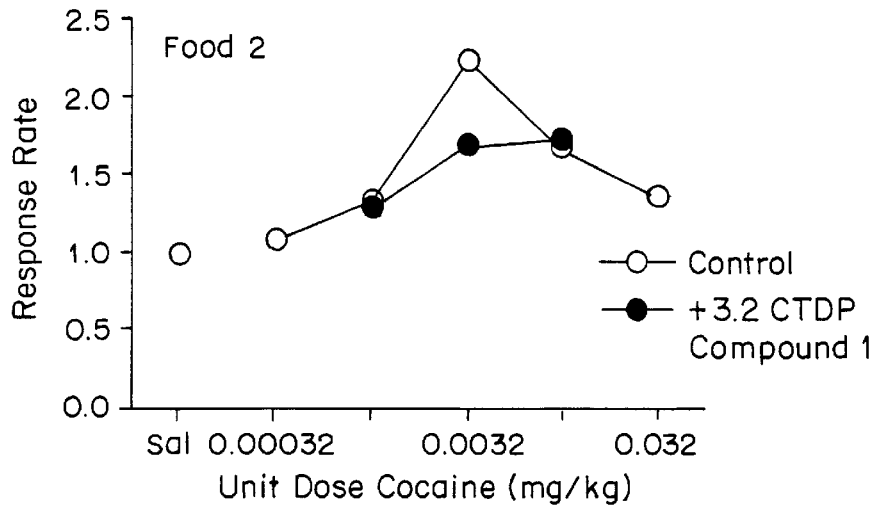
Figure 26A:
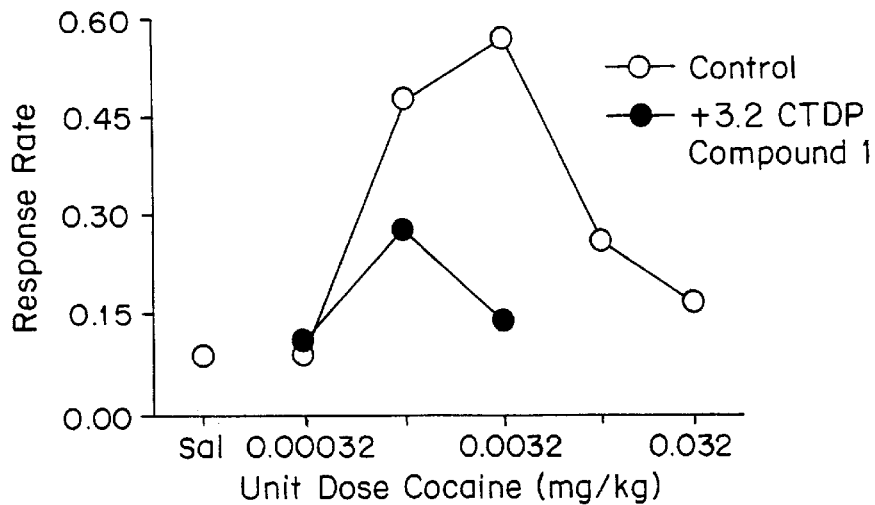
FIG. 26A through 26C are graphs showing the effects of Compound 1 on the complete cocaine dose-effect curve in monkey J3A. The graph shows the unit dose cocaine available during the drug component in mg/kg/injection versus response rate in responses/sec. Panels show data from the drug component (top panel), first food component (middle panel) and second food component (bottom panel) (see Example 7).
Figure 26B:
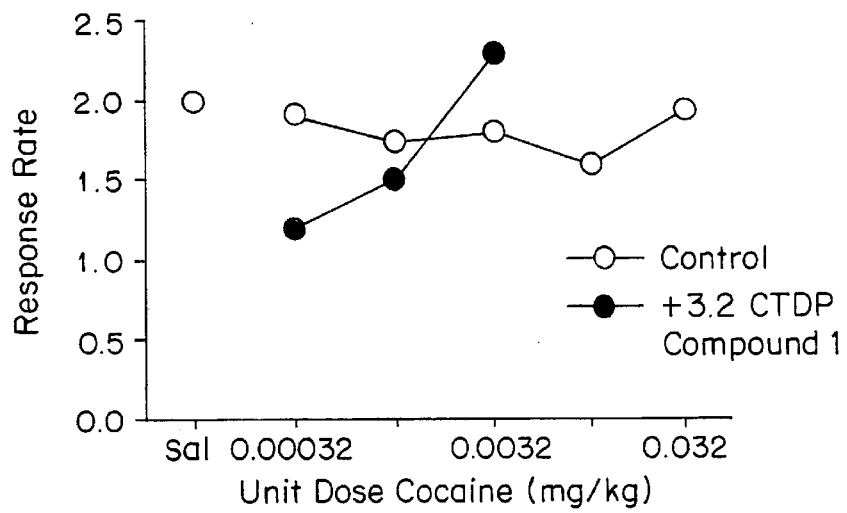
Figure 26C:
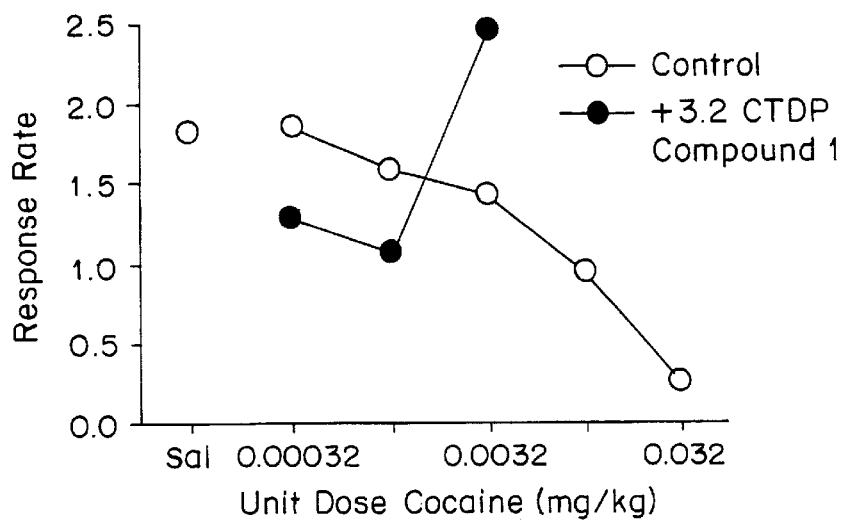

FIGS. 24–26 show the effect of 3.2 mg/kg Compound 1 on the complete cocaine dose-effect curves in monkeys 89B056, WH8 and J3A. The top panel in each figure shows response rates during the drug component, the middle panel shows response rates during the first food component (prior to the drug component), and the bottom panel shows response rates during the second food component (following the drug component). Under control conditions (i.e. no pretreatment), the dose-effect curve for cocaine self-administration had an inverted-U shape, with maximal rates of cocaine self-administration maintained by unit doses of 0.0032 mg/kg/inj cocaine (monkeys 89B056 and J3A) or 0.01 mg/kg/inj cocaine (monkey WH8). Rates of food-maintained responding were always higher than rates of cocaine self-administration, and across the range of cocaine doses examined, rates of food-maintained responding during the two food components were usually independent of the unit dose of cocaine. The only exception to this general finding occurred in monkey J3A, in which rates of food-maintained responding during the second food component decreased as the unit dose of cocaine available during the drug component increased.

Pretreatment with 3.2 mg/kg Compound 1 decreased rates of cocaine self-administration across a wide range of cocaine unit doses while producing relatively minor effects on food-maintained responding in all three monkeys. In monkey 89B056, 3.2 mg/kg Compound 1 decreased rates of cocaine self-administration maintained by cocaine unit doses ranging from 0.0032 to 0.032 mg/kg/inj (FIG. 24). Rates of food-maintained responding were usually unaffected by 3.2 mg/kg Compound 1 in monkey 89B056. In monkey WH8, 3.2 mg/kg Compound 1 decreased rates of cocaine self-administration maintained by cocaine unit doses of 0.001–0.01 mg/kg/inj (FIG. 25). Compound 1 decreased rates of food-maintained responding to approximately 30% of control levels during the first food component in monkey WH8, but response rates during the second food component were unaffected. In monkey J3A, Compound 1 decreased responding maintained by 0.001 and 0.0032 mg/kg/inj cocaine and produced small and inconsistent changes in rates of food-maintained responding (FIG. 26).

Across the dose range tested, Compound 1 did not produce noticeable overt behavioral effects prior to or during the test session. In addition, Compound 1 usually had no effect on operant response rates on the day following its administration. On some occasions, however, response rates during the food and/or drug components were altered on the day following administration of Compound 1.

DISCUSSION

Compound 1 (0.1–3.2 mg/kg) dose-dependently decreased rates of cocaine self-administration maintained by a unit dose of cocaine located at the peak of the cocaine dose-effect curve in each of four monkeys tested. In addition, 3.2 mg/kg Compound 1 decreased rates of cocaine self-administration across a one to two log unit range of cocaine doses in each of three monkeys tested. Doses of Compound 1 that decreased rates of cocaine self-administration usually decreased rates of food-maintained responding less or increased rates of food-maintained responding. In addition, these doses of Compound 1 did not produce noticeable overt behavioral effects. These findings suggest that Compound 1 can produce selective decreases in cocaine self-administration maintained by a wide range of cocaine unit doses while producing a profile of relatively mild undesirable side effects.

It is of interest to compare the results of the present study with the results of our previous evaluation of Compound 1 in Task I: Drug Discrimination. In that study, doses of Compound 1 up to 1.0 mg/kg had little or no effect on response rates, and a dose of 3.2 mg/kg Compound 1 had little effect on response rates in two monkeys, increased response rates in one monkey, and eliminated responding in only one monkey. These results agree with the present study in finding that doses of Compound 1 up to 3.2 mg/kg usually have little effect on rates of food-maintained responding and may increase rates of food-maintained responding. Higher doses of Compound 1 were not examined in the present study. However, it should be noted that a higher dose of 10 mg/kg Compound 1 was administered to one monkey in our previous drug discrimination study, and this dose of Compound 1 eliminated operant responding, decreased free feeding and produced overt behavioral effects including hyperactivity and agitation for several days. Thus, while doses of Compound 1 up to 3.2 mg/kg may produce relatively selective decreases in cocaine self-administration, higher doses may produce severe and protracted toxic effects.

EQUIVALENTS

Those skilled in the art will know, or be able to ascertain using no more than routine experimentation, many equivalents to the specific embodiments of the invention described herein. These and all other equivalents are intended to be encompassed by the following claims.

What is claimed is:

1. A method of treating an individual for cocaine abuse, comprising administering to the individual a therapeutically effective amount of a compound or mixture of compounds represented by the following structural formula:

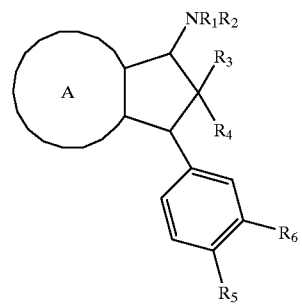

wherein:

Ring A is selected from the group consisting of an aryl group and a substituted aryl group;

R1 and R2 are independently selected from the group consisting of a lower alkyl group and a substituted lower alkyl group;

R3 and R4 are independently selected from the group consisting of —H, a lower alkyl group and substituted lower alkyl; and R5 and R6 are independently selected from the group consisting of —H, halogen, an alkyl group, a substituted alkyl group, hydroxy, (lower alkyl)-O—, (substituted lower alkyl)-O—, —CN, —NO$_2$, amine, (lower alkyl) amine, (substituted lower alkyl) amine, (di-lower alkyl) amine and (substituted di-lower alkyl) amine.

2. A viewfinder optical system as claimed in claim 1, wherein said relay lens system comprises a single lens element having positive optical power.

3. A viewfinder optical system as claimed in claim 1, wherein the entire viewfinder optical system comprises three lenses.

4. The method of claim 3 wherein R5 and R6 are each a halogen and R1 and R2 are each a C1 to C3 straight chained alkyl.

5. The method of claim 4 where R3 and R4 are each —H.

6. The method of claim 1 wherein the compound is represented by the following structural formula:

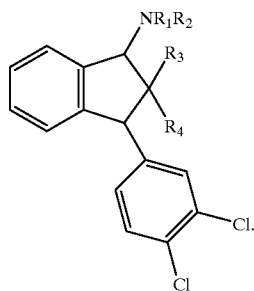

7. The method of claim 6 wherein R3 and R4 are each —H.

8. The method of claim 7 wherein the compound has trans stereochemistry.

9. The method of claim 8 wherein R1 is methyl and R2 is selected from the group consisting of methyl, ethyl and n-propyl.

10. The method of claim 8 wherein R1 is methyl and R2 is a C1–C4 straight or branched chain hydrocarbon.

11. A method of treating an individual with Parkinson's disease or attention deficit hyperactivity disorder, comprising administering to the individual a therapeutically effective amount of a compound or mixture of compounds represented by the following structural formula:

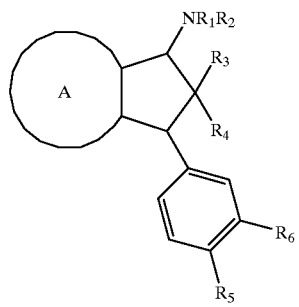

wherein:

Ring A is selected from the group consisting of an aryl group and a substituted aryl group;

R1 and R2 are independently selected from the group consisting of a lower alkyl group and a substituted lower alkyl group;

R3 and R4 are independently selected from the group consisting of —H, a lower alkyl group and substituted lower alkyl; and R5 and R6 are independently selected from the group consisting of —H, halogen, an alkyl group, a substituted alkyl group, hydroxy, (lower alkyl)-O—, (substituted lower alkyl)-O—, —CN, —NO$_2$, amine, (lower alkyl) amine, (substituted lower alkyl) amine, (di-lower alkyl) amine and (substituted di-lower alkyl) amine.

12. The method of claim 11 wherein Ring A is selected from the group consisting of phenyl and naphthyl.

13. The method of claim 11 wherein Ring A is phenyl.

14. The method of claim 13 wherein R5 and R6 are each a halogen and R1 and R2 are each C1 to C3 straight chained alkyl.

15. A viewfinder optical system including at least two surfaces having optical power of diffraction refraction, wherein the optical power of refraction of said surfaces is equivalent to that of an aspherical surfaces.

16. The method of claim 11 wherein the compound is represented by the following structural formula:

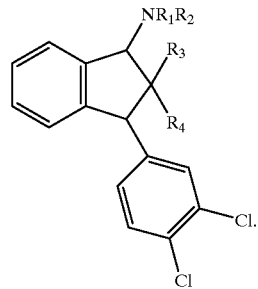

17. A Kepler-type viewfinder optical system as claimed in claim 16, wherein said eyepiece optical system comprises a single lens element.

18. The method of claim 17 wherein the compound has trans stereochemistry.

19. The method of claim 18 wherein R1 is methyl and R2 is selected from the group consisting of methyl, ethyl and n-propyl.

20. The method of claim 18 wherein R1 is methyl and R2 is a C1–C4 straight or branched chain hydrocarbon.

21. A method of treating an individual for cocaine abuse, comprising administering to the individual a therapeutically effective amount of a compound or mixture of compounds represented by the following structural formula:

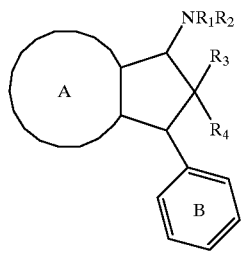

wherein:

Ring A is selected from the group consisting of an aryl group and a substituted aryl group;

Ring B is unsubstituted or substituted with one, two or three substituents other than hydrogen that are each, independently, selected from the group consisting of a halogen, an alkyl group, a substituted alkyl group, hydroxy, (lower alkyl)-O—, (substituted lower alkyl)-O—, —CN, —NO$_2$, amine, (lower alkyl) amine, (substituted lower alkyl) amine, (di-lower alkyl) amine and (substituted di-lower alkyl) amine;

R1 is selected from the group consisting of a lower alkyl group and a substituted lower alkyl group;

R2 is selected from the group consisting of a lower alkyl group, a substituted lower alkyl group, —(CH$_2$)$_n$-aryl and —(CH$_2$)$_n$-(substituted aryl);

n is an integer from one to about three; and

R3 and R4 are independently selected from the group consisting of —H, a lower alkyl group and substituted lower alkyl.

22. The method of claim 21 wherein:

Ring A is phenyl;

R1 is methyl;

R2 is benzyl or substituted benzyl;

R3 and R4 are each —H; and
the compound has trans stereochemistry.

23. The method of claim 21 wherein the compound is represented by the following structural formula:

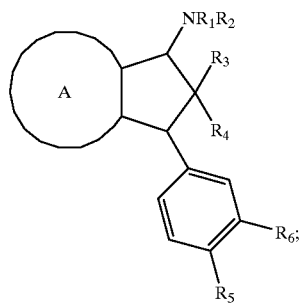

wherein R5 and R6 are independently selected from the group consisting of —H, halogen, an alkyl group, a substituted alkyl group, hydroxy, (lower alkyl)-O—, (substituted lower alkyl)-O—, —CN, —NO$_2$, amine, (lower alkyl) amine, (substituted lower alkyl) amine, (di-lower alkyl) amine and (substituted di-lower alkyl) amine.

24. The method of claim 23 wherein R2 is benzyl and R5 and R6 are each —Cl.

25. A method of treating an individual with Parkinson's disease or attention deficit hyperactivity disorder, comprising administering to the individual a therapeutically effective amount of a compound or mixture of compounds represented by the following structural formula:

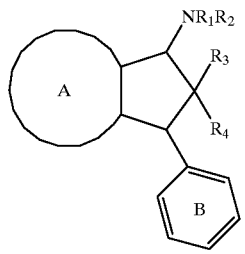

wherein:
Ring A is selected from the group consisting of an aryl group and a substituted aryl group;
Ring B is unsubstituted or substituted with one, two or three substituents other than hydrogen that are each, independently, selected from the group consisting of a halogen, an alkyl group, a substituted alkyl group, hydroxy, (lower alkyl)-O—, (substituted lower alkyl)-O—, —CN, —NO$_2$, amine, (lower alkyl) amine, (substituted lower alkyl) amine, (di-lower alkyl) amine and (substituted di-lower alkyl) amine;

R1 is selected from the group consisting of a lower alkyl group and a substituted lower alkyl group;
R2 is selected from the group consisting of a lower alkyl group, a substituted lower alkyl group, —(CH$_2$)$_n$-aryl and —(CH$_2$)$_n$-(substituted aryl);
n is an integer from one to about three; and
R3 and R4 are independently selected from the group consisting of —H, a lower alkyl group and substituted lower alkyl.

26. A method of treating an individual who abuses cocaine, an individual with Parkinson's disease or an individual with attention deficit hyperactivity disorder, comprising administering to the individual a compound or mixture of compounds represented by the following structural formula:

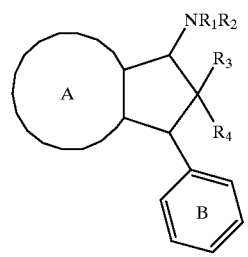

27. A method of treating an individual who abuses cocaine, an individual with Parkinson's disease or an individual with attention deficit hyperactivity disorder, comprising administering to the individual a compound or mixture of compounds represented by the following structural formula:

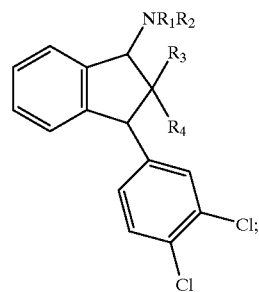

wherein:
R1 and R2 are each methyl; and
R3 and R4 are each —H.

* * * * *

UNITED STATES PATENT AND TRADEMARK OFFICE
CERTIFICATE OF CORRECTION

PATENT NO. : 6,011,070
DATED : January 4, 2000
INVENTOR(S) : Mark Froimowitz and Kuo-Ming Wu It is certified that error appears in the above-indentified patent and that said Letters Patent is hereby corrected as shown below:

Delete text of Claim 2 and substitute therefor --The method of Claim 1 wherein Ring A is selected from the group consisting of phenyl and naphthyl.--

Delete text of Claim 3 and substitute therefor --The method of Claim 1 wherein Ring A if phenyl.--

Delete text of Claim 15 and substitute therefor --The method of Claim 14 wherein R3 and R4 are each -H.--

Delete text of Claim 17 and substitute therefor --The method of Claim 16 wherein R3 and R4 are each -H.--

At Claim 26, following the structure, insert:

--wherein:

Ring A is selected from the group consisting of an aryl group and a substituted aryl group;

Ring B is unsubstituted or substituted with one, two or three substituents other than hydrogen that are each, independently, selected from the group consisting of a halogen, an alkyl group, a substituted alkyl group, hydroxy, (lower alkyl)-O-, (substituted lower alkyl)-O-, -CN, -$NO_2$, amine, (lower alkyl) amine, (substituted lower alkyl) amine, (di-lower alkyl) amine and (substituted di-lower alkyl) amine;

R1 is selected from the group consisting of a lower alkyl group and a substituted lower alkyl group;

R2 is selected from the group consisting of a lower alkyl group, a substituted lower alkyl group, -$(CH_2)_n$-aryl and -$(CH_2)_n$-(substituted aryl);

n is an integer from one to about three; and

UNITED STATES PATENT AND TRADEMARK OFFICE
CERTIFICATE OF CORRECTION

PATENT NO. : 6,011,070
DATED : January 4, 2000
INVENTOR(S) : Mark Froimowitz and Kuo-Ming Wu It is certified that error appears in the above-identified patent and that said Letters Patent is hereby corrected as shown below:

R3 and R4 are independently selected from the group consisting of -H, a lower alkyl group and substituted lower alkyl.--

Signed and Sealed this

Twenty-first Day of November, 2000

Attest:

Q. TODD DICKINSON

*Attesting Officer*          *Director of Patents and Trademarks*